(12) United States Patent
Hahn et al.

(10) Patent No.: US 7,351,797 B1
(45) Date of Patent: Apr. 1, 2008

(54) LABELED PEPTIDES, AND PROCESSES AND INTERMEDIATES USEFUL FOR THEIR PREPARATION

(75) Inventors: Klaus M. Hahn, San Diego, CA (US); Steven J. Bark, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/381,903

(22) PCT Filed: Sep. 29, 2000

(86) PCT No.: PCT/US00/26821

§ 371 (c)(1),
(2), (4) Date: Aug. 20, 2003

(87) PCT Pub. No.: WO02/28890

PCT Pub. Date: Apr. 11, 2002

(51) Int. Cl.
*C07K 14/00* (2006.01)
*A61K 39/395* (2006.01)

(52) U.S. Cl. .................. 530/350; 530/300; 530/345; 530/405; 530/406; 530/412; 424/193.1; 424/178.1

(58) Field of Classification Search .............. 530/345, 530/350, 300, 405, 406, 412; 424/193.1, 424/178.1
See application file for complete search history.

(56) References Cited

U.S. PATENT DOCUMENTS

| 3,862,111 A | 1/1975 | Low et al. | |
| 5,880,270 A | 3/1999 | Berninger et al. | ....... 530/391.1 |
| 6,001,364 A | 12/1999 | Rose et al. | |

FOREIGN PATENT DOCUMENTS

| WO | WO-9640662 A2 | 12/1996 |
| WO | WO 0075105 A1 | 12/2004 |

OTHER PUBLICATIONS

Bark et al., J. Am. Chem. Soc. 122 (15), 3567-3573 (Apr. 2000).*
Peri et al., Tetrahedron 54, 12269-12278 (1998).*
Bark, S. J., et al., "A Hightly Efficient Method for Site-Specific Modification of Unprotected Peptides after Chemical Synthesis", *Journal of the American Chemical Society*, 122, (Apr. 19, 2000),3567-3573.
Cervigni, S. E., et al., "Synthesis of Glycopeptides and Lipopeptides by Chemoselective Ligation", *Angew. Chem. Int. Ed. Engl.*, 35, (1996),1230-1232.
Chamberlain, C., et al., "Watching Proteins in the Wild: Fluorescence Methods to Study Protein Dynamics in Living Cells", *Traffic*, 1, (2000),755-762.
Gaertner, H. F., et al., "Site-Specific Attachment of Functionalized Poly(ethylene glycol) to the Amino Terminus of Proteins", *Bioconjugate Chem.* 7, (1996),38-44.

Lelievre, D., et al., "Simple and Efficient Solid-Phase Synthesis of Unprotected Peptide Aldehyde for Peptide Segment Ligation", *Tetrahedron Letters*, 39, (1998),9675-9678.
Whish, W. J., et al., "Studies on the Aminoxyalanine Methyl Ester and Its alpha-N-acetyl Derivative", *Canadian Journal of Biochemistry*, 48, (1970),520-522.
Adamczyk, M., et al., "A Chemoselective Method for Site-Specific Immobilization of Peptides via Aminooxy Group", *Bioconjugate Chemistry*, 12, (Feb. 28, 2001),139-142.
Bark, Steven J., et al., "A Highly Efficient Method for Site-Specific Modification of Unprotected Peptides After Chemical Synthesis", *Journal of American Chemical Society*, 122(15), (Apr. 19, 2000); pp. 3567-3573.
Cervigni, Stefano E., et al., "Synthesis of Glycopeptides and Lipopeptides by Chemselective Ligation", *Angew. Chem. Int. Ed. Engl.*, 35(11), (Jun. 17, 1996); pp. 1230-1232.
Valeur, Bernard, *Molecular Fluorescence—Principles and Applications*, Copyright 2002, Wiley-VCH Verlag GmbH, 69469 Weinhem, Germany; ISBN 3-527-29919-X; pp. 200, 202, 276, 322 and 334.
Whish, W. J., et al., "Studies on the aminoxyalanine methyl ester and its alpha-N-acetyl derivative", *Canadian Journal of Biochemistry*, 48(4), (Apr. 1970); pp. 520-522.

(Continued)

*Primary Examiner*—Chih-Min Kam
(74) *Attorney, Agent, or Firm*—Schwegman, Lundberg & Woessner, P.A.

(57) ABSTRACT

The invention provides intermediates and methods that allow for site-specific modification of peptides after synthesis. Accordingly, functional molecules can be selectively linked to a peptide to provide a peptide conjugate having altered biological, chemical, or physical properties. For example, functional molecules (e.g. biophysical probes, peptides, polynucleotides, and therapeutic agents) can be linked to a peptide to provide a peptide conjugate having differing and useful properties. The invention also provides a compound of formula (III):

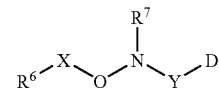

wherein:

$R^6$ is a peptide;

X is a direct bond or a linking group;

$R^7$ is hydrogen, $(C_1\text{-}C_6)$alkyl, an amino protecting group, or a radical comprising one or more aminooxy groups;

Y is a direct bond or a linking group; and

D is a functional molecule.

21 Claims, 4 Drawing Sheets

OTHER PUBLICATIONS

Baumann, O., et al., "Laser confocal scanning microscopy of the surface membrane/T-tubular system and the sarcoplasmic reticulum in insect striated muscle stained with DilC18(3).", *J Struct Biol.*, 105(1-3), (Oct.-Dec. 1990),154-61.

Gee, K, R., "Novel fluorogenic substrates for acid phosphatase", *Bioorg Med Chem Lett.*, 9(10), (May 17, 1999),1395-6.

Geoghegan, K. F., et al., "Site-directed conjugation of non-peptide groups to peptides and proteins via periodate oxidation of a 2-amino alcohol. Application to modification at N-terminal serine.", *Bioconjugate*, 3(2), (Mar.-Apr. 1992), 138-146.

Grynkiewicz, G., et al., "A new generation of Ca2+ indicators with greatly improved fluorescence properties", *J Biol Chem.*, 260(6), (Mar. 25, 1985),3440-3450.

Merritt, J. E., et al., "Use of fluo-3 to measure cytosolic Ca2+ in platelets and neutrophils. Loading cells with the dye, calibration of traces, measurements in the presence of plasma, and buffering of cytosolic Ca2+.", *Biochem J.*, 269(2), (Jul. 15, 1990),513-519.

Minta, A, et al., "Fluorescent indicators for cytosolic calcium based on rhodamine and fluorescein chromophores", *J Biol Chem.*, 264(14), (May 15, 1989),8171-8178.

Orte, A., et al., "Absorption and Emission Study of 2',7'-Difluorofluorescein and Its Excited-State Buffer-Mediated Proton Exchange Reactions", *The Journal of Physical Chemistry A*, 109(5), (Feb. 10, 2005),734-747.

Stewart, W. W., "Functional connections between cells as revealed by dye-coupling with a highly fluorescent naphthalimide tracer", *Cell*, 14(3), (July, 1978),741-59.

Stewart, W. W., "Lucifer dyes—highly fluorescent dyes for biological tracing", *Nature*, 292, (Jul. 2, 1981),17-21.

Vilaseca, L. A., et al., "Protein conjugates of defined structure: synthesis and use of a new carrier molecule", *Bioconjugate Chem.*, 4(6), (Nov.-Dec. 1993),515-520.

Whitaker, J., et al., "Cascade Blue derivatives: Water soluble, reactive, Blue emission dyes evaluated as fluorescent labels and tracers", *Analytical Biochemistry*, 198(1), (Oct. 1991),119-130.

Zucker, R. S., "Effects of photolabile calcium chelators on fluorescent calcium indicators", *Cell Calcium*, 13(1), (Jan. 1992),29-40.

\* cited by examiner

SEQUENCE LISTING

```
<160> NUMBER OF SEQ ID NOS: 12

<210> SEQ ID NO 1
<211> LENGTH: 44
<212> TYPE: PRT
<213> ORGANISM: Homo sapiens

<400> SEQUENCE: 1

Lys Lys Lys Glu Lys Glu Arg Pro Glu Ile Ser Leu Pro Ser Asp Phe
 1               5                  10                  15

Glu His Thr Ile His Val Gly Phe Asp Ala Cys Thr Gly Glu Phe Thr
            20                  25                  30

Gly Met Pro Glu Gln Trp Ala Arg Leu Leu Gln Thr
        35                  40

<210> SEQ ID NO 2
<211> LENGTH: 16
<212> TYPE: PRT
<213> ORGANISM: Artificial Sequence
<220> FEATURE:
<221> NAME/KEY: SITE
<222> LOCATION: 10
<223> OTHER INFORMATION: a modified residue
<220> FEATURE:
<223> OTHER INFORMATION: a synthetic peptide

<400> SEQUENCE: 2

Ala Lys Ala Ala Arg Ala Ala Ala Ala Xaa Ala Ala Arg Ala Cys Ala
 1               5                  10                  15

<210> SEQ ID NO 3
<211> LENGTH: 9
<212> TYPE: PRT
<213> ORGANISM: Artificial Sequence
<220> FEATURE:
<221> NAME/KEY: SITE
<222> LOCATION: 3
<223> OTHER INFORMATION: a protected N-methylaminooxy amino acid
<220> FEATURE:
<223> OTHER INFORMATION: a synthetic peptide

<400> SEQUENCE: 3

Leu Tyr Xaa Ala Gly Met Pro Ala Leu
 1               5

<210> SEQ ID NO 4
<211> LENGTH: 5
```

```
<212> TYPE: PRT
<213> ORGANISM: Homo sapiens

<400> SEQUENCE: 4

Lys Asn Ala Arg Cys
 1               5

<210> SEQ ID NO 5
<211> LENGTH: 10
<212> TYPE: PRT
<213> ORGANISM: Artificial Sequence
<220> FEATURE:
<221> NAME/KEY: SITE
<222> LOCATION: 8
<223> OTHER INFORMATION: a protected N-methylaminooxy amino acid
<220> FEATURE:
<223> OTHER INFORMATION: a synthetic peptide

<400> SEQUENCE: 5

Lys Asn Ala Arg Cys Gly Ala Xaa Tyr Leu
 1               5                  10

<210> SEQ ID NO 6
<211> LENGTH: 33
<212> TYPE: PRT
<213> ORGANISM: Artificial Sequence
<220> FEATURE:
<223> OTHER INFORMATION: a synthetic peptide

<400> SEQUENCE: 6

Cys Glu Tyr Arg Ile Asp Arg Val Arg Leu Phe Val Asp Lys Leu Asp
 1               5                  10                  15

Asn Ile Ala Gln Val Pro Arg Val Gly Ala Ala His His His His His
            20                  25                  30

His

<210> SEQ ID NO 7
<211> LENGTH: 33
<212> TYPE: PRT
<213> ORGANISM: Artificial Sequence
<220> FEATURE:
<223> OTHER INFORMATION: a synthetic peptide

<400> SEQUENCE: 7

Cys Glu Tyr Arg Ile Asp Arg Val Arg Leu Phe Val Asp Lys Leu Asp
 1               5                  10                  15

Asn Ile Ala Gln Val Pro Arg Val Gly Ala Ala His His His His His
            20                  25                  30

His

<210> SEQ ID NO 8
<211> LENGTH: 31
<212> TYPE: PRT
<213> ORGANISM: Artificial Sequence
<220> FEATURE:
<221> NAME/KEY: SITE
<222> LOCATION: 1
<223> OTHER INFORMATION: a protected N-methylaminooxy amino acid
<220> FEATURE:
<223> OTHER INFORMATION: a synthetic peptide

<400> SEQUENCE: 8

Xaa Lys Lys Lys Glu Lys Glu Arg Pro Glu Ile Ser Leu Pro Ser Asp
 1               5                  10                  15

Phe Glu His Thr Ile His Val Gly Phe Asp Ala Met Pro Ala Leu
```

```
                    20                  25                  30

<210> SEQ ID NO 9
<211> LENGTH: 18
<212> TYPE: PRT
<213> ORGANISM: Homo sapiens

<400> SEQUENCE: 9

Cys Thr Gly Glu Phe Thr Gly Met Pro Glu Gln Trp Ala Arg Leu Leu
 1               5                  10                  15

Gln Thr

<210> SEQ ID NO 10
<211> LENGTH: 10
<212> TYPE: PRT
<213> ORGANISM: Artificial Sequence
<220> FEATURE:
<223> OTHER INFORMATION: a synthetic peptide
<220> FEATURE:
<221> NAME/KEY: SITE
<222> LOCATION: 8
<223> OTHER INFORMATION: a protected N-methylaminooxy amino acid

<400> SEQUENCE: 10

Lys Asn Ala Arg Cys Gly Ala Xaa Tyr Leu
 1               5                  10

<210> SEQ ID NO 11
<211> LENGTH: 45
<212> TYPE: PRT
<213> ORGANISM: Artificial Sequence
<220> FEATURE:
<223> OTHER INFORMATION: a synthetic peptide
<220> FEATURE:
<221> NAME/KEY: SITE
<222> LOCATION: 1
<223> OTHER INFORMATION: a protected N-methylaminooxy amino acid

<400> SEQUENCE: 11

Xaa Lys Lys Lys Glu Lys Glu Arg Pro Glu Ile Ser Leu Pro Ser Asp
 1               5                  10                  15

Phe Glu His Thr Ile His Val Gly Phe Asp Ala Cys Thr Gly Glu Phe
                20                  25                  30

Thr Gly Met Pro Glu Gln Trp Ala Arg Leu Leu Gln Thr
            35                  40                  45

<210> SEQ ID NO 12
<211> LENGTH: 38
<212> TYPE: PRT
<213> ORGANISM: Artificial Sequence
<220> FEATURE:
<223> OTHER INFORMATION: a synthetic peptide
<220> FEATURE:
<221> NAME/KEY: SITE
<222> LOCATION: 3
<223> OTHER INFORMATION: a protected N-methylaminooxy amino acid

<400> SEQUENCE: 12

Leu Tyr Xaa Ala Gly Cys Glu Tyr Arg Ile Asp Arg Val Arg Leu Phe
 1               5                  10                  15

Val Asp Lys Leu Asp Asn Ile Ala Gln Val Pro Arg Val Gly Ala Ala
                20                  25                  30

His His His His His His
            35
```

LABELED PEPTIDES, AND PROCESSES AND INTERMEDIATES USEFUL FOR THEIR PREPARATION

GOVERNMENT FUNDING

The invention described herein was made with United States Government support under Grant Number MCB-9812248 awarded by the National Science Foundation, and under Grant Numbers CA58689 and GM 57464 awarded by the National Institutes of Health. The United States Government has certain rights in this invention.

RELATED APPLICATION AND CLAIM OF PRIORITY

This is a U.S. National Stage application under 35 U.S.C. 371, from PCT/US00/26821 filed 29 Sep. 2000 and published in English on 11 Apr. 2002 as International Publication Number WO 02/28890 A1, which application and publication are incorporated herein by reference.

BACKGROUND OF THE INVENTION

Modified peptides and proteins are valuable biophysical tools for studying biological processes, both in vitro and in vivo. They are also useful in assays to identify new drugs and therapeutic agents. In particular, quantitative live cell imaging using fluorescent proteins and peptides is revolutionizing the study of cell biology. An exciting recent development within this field has been the construction of peptide and protein biosensors exhibiting altered fluorescence properties in response to changes in their environment, oligomeric state, conformation upon ligand binding, structure, or direct ligand binding. Appropriately labeled fluorescent biomolecules allow spatial and temporal detection of biochemical reactions inside living cells. See for example Giuliano, K. A., et al., *Annu. Rev. Biophys. Biomol. Struct.* 1995,24:405-434; Day, R. N. *Mol. Endocrinol.* 1998, 12:1410-9; Adams, S. R., et al., *Nature* 1991, 349:694; Miyawaski, A., et al., *Nature* 1997, 388:882-7; Hahn, K., et al., *Nature* 1992, 359:736; Hahn, K. M., et al., *J. Biol. Chem.* 1990,265: 20335; and Richieri, G. V., et al., *Mol. Cell. Biochem.* 1999, 192:87-94.

Procedures for site-specific modification of polypeptides have been described, including: chemically selective labeling in solution Brinkley, M. *Bioconjugate Chemistry* 1992, 3:2-13) and on resin bound peptides (Hackeng, T., et al., *J. Biol. Chem.* Submitted); introduction of ketone amino acids through synthetic procedures (Rose, K. *J. Am. Chem. Soc.* 1994, 116:30-33; King, T. P., et al., *Biochemistry,* 1986, 25:57745779; Rose, K., et al., *Bioconjugate Chem.* 1996, 7:552-556; Marcaurelle, L. A., Bertozzi, C. R. Tett. Lett. 1998, 39:7279-7282; and Wahl, F., Mutter, M. Tett. Lett. 1996, 37:6861-6864); and molecular biology techniques (Cornish, V. W., et al., *J. Am. Chem. Soc.* 1996, 118:8150).

While each of these methods has utility for producing a particular class of biosensor or labeled polypeptide, all have limitations that restrict their general use. Labeling of natural amino acid sidechains in solution is often impractical because of the existence of many other competing nucleophiles. Additionally, the use of unnatural amino acids, such as those bearing ketones for selective labeling, requires the synthesis of dye constructs or amino acids that are difficult to make and not available commercially.

Currently, the major obstacles to the development of fluorescent biosensors remain: (1) The difficulty in site-specific placement of the dye in the polypeptide and (2) determining exactly which site is optimal for dye placement (Giuliano, K. A., et al., *Annu. Rev. Biophys. Biomol. Struct.* 1995, 24:405-434). Solvent-sensitive dyes and other biophysical probes must be placed precisely for optimal response to changes in protein structure without interference with biological activity. Also, the need for site-specific incorporation of two dyes without impairment of biological activity has proven a serious limitation for utilization of fluorescence resonance energy transfer (FRET) within a single protein. Total chemical synthesis of proteins provides a potential solution to these problems (Wilken, J., Kent, S. B. H. *Curr. Op. Biotechnology.* 1998, 9:412; Kent, S. B. H. *Ann. Rev. Biochem.* 1988, 57, 957-989; Dawson, P. E., et al., *Science* 1994, 266:776-779; Muir, T. W., et al., *Proc. Natl. Acad. Sci.* 1998, 95:6705-6710; and Cotton, G. J., et al., *J. Ann. Chem. Soc.* 1999, 121:1100-1101). However, many biophysical probes suitable for fluorescent biosensors or other purposes are not stable to the various conditions used for peptide synthesis, and site-specific incorporation after synthesis is difficult to achieve.

Thus, there is currently a need for peptide synthons having protected functional groups that can be selectively modified to incorporate one or more functional molecules (e.g. a biophysical probe such as a fluorescent label) following peptide synthesis.

SUMMARY OF THE INVENTION

A highly efficient method for the site-specific attachment of biophysical probes or other molecules to unprotected peptides following chemical synthesis has been developed. The methodology utilizes amino acids having one or more protected aminooxy groups, which can be incorporated during solid-phase peptide synthesis or which can be combined with recombinant peptides through post expression steps. It has been discovered that the protected aminooxy group can be unmasked following peptide synthesis, and reacted with an electrophilic reagent to provide a modified (e.g. a labeled) peptide. The aminooxy group reacts selectively with electrophiles (e.g. an activated carboxylic ester such as an N-hydroxysuccinimide ester) in the presence of other nucleophilic groups including cysteine, lysine and amino groups.

Thus, selective peptide modification (e.g. labeling) can be accomplished after synthesis using commercially available and/or chemically sensitive molecules (e.g. probes). The methodology is compatible with the synthesis of C-thioester containing peptides and amide-forming ligations, required steps for the synthesis of proteins by either total chemical synthesis or expressed protein ligation. An aminooxy containing amino acid can be introduced into different sites by parallel peptide synthesis to generate a polypeptide analogue family with each member possessing a single specifically-labeled site. The parallel synthesis enables the development of optimized biosensors or other modified polypeptides through combinatorial screening of different attachment sites for maximal response and minimal perturbation of desired biological activity.

Thus, a simple and efficient methodology for site-specific modification (e.g. labeling) of peptides after synthesis has been developed that provides high yield, selectivity, and compatibility with both solid-phase peptide synthesis and $C^\alpha$-thioester peptide recombinant synthesis.

Accordingly, the invention provides a synthetic intermediate (i.e. a synthon) useful for preparing modified peptides, which is a compound of formula (I):

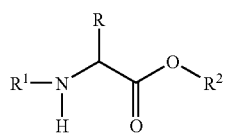

wherein:

R¹ is hydrogen or an amino protecting group;

R² is hydrogen or a carboxy protecting group;

R is an organic radical comprising one or more aminooxy groups.

Peptides including one or more aminooxy groups are also useful synthetic intermediates that can be modified to provide related peptides having altered biological, chemical, or physical properties, such as, for example, a peptide linked to a fluorescent label. Accordingly, the invention also provides a peptide having one or more (e.g. 1, 2, 3, or 4) aminooxy groups; provided the peptide is not glutathione. The invention also provides a peptide having one or more (e.g. 1, 2, 3, or 4) secondary aminooxy groups.

The invention generally provides intermediates and methods that allow for site-specific modification of peptides after synthesis. Accordingly, functional molecules can be selectively linked to a peptide to provide a peptide conjugate having altered biological, chemical, or physical properties. For example, functional molecules (e.g. biophysical probes, peptides, polynucleotides, and therapeutic agents) can be linked to a peptide to provide a peptide conjugate having differing and useful properties. Thus, the invention also provides a compound of formula (III):

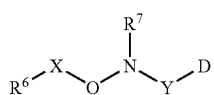

wherein:

R⁶ is a peptide;

X is a direct bond or a linking group;

R⁷ is hydrogen, ($C_1$-$C_6$)alyl, an amino protecting group, or a radical comprising one or more aminooxy groups;

Y is a direct bond or a linking group; and

D is a functional molecule.

Preferably the functional molecule is a biophysical probe, such as a fluorescent group that can be used for FRET studies or other studies involving fluorescent signals, such as excimer pair formation.

Processes for preparing synthons of the invention as well as the protein conjugates of the invention are provided as further embodiments of the invention and are illustrated by the procedures in the Examples below.

Thus, the invention also provides a method for preparing a peptide conjugate comprising a peptide and a functional molecule, comprising reacting a peptide having one or more aminooxy groups with a corresponding functional molecule having an electrophylic moiety, to provide the peptide conjugate.

DETAILED DESCRIPTION

Figure 1:
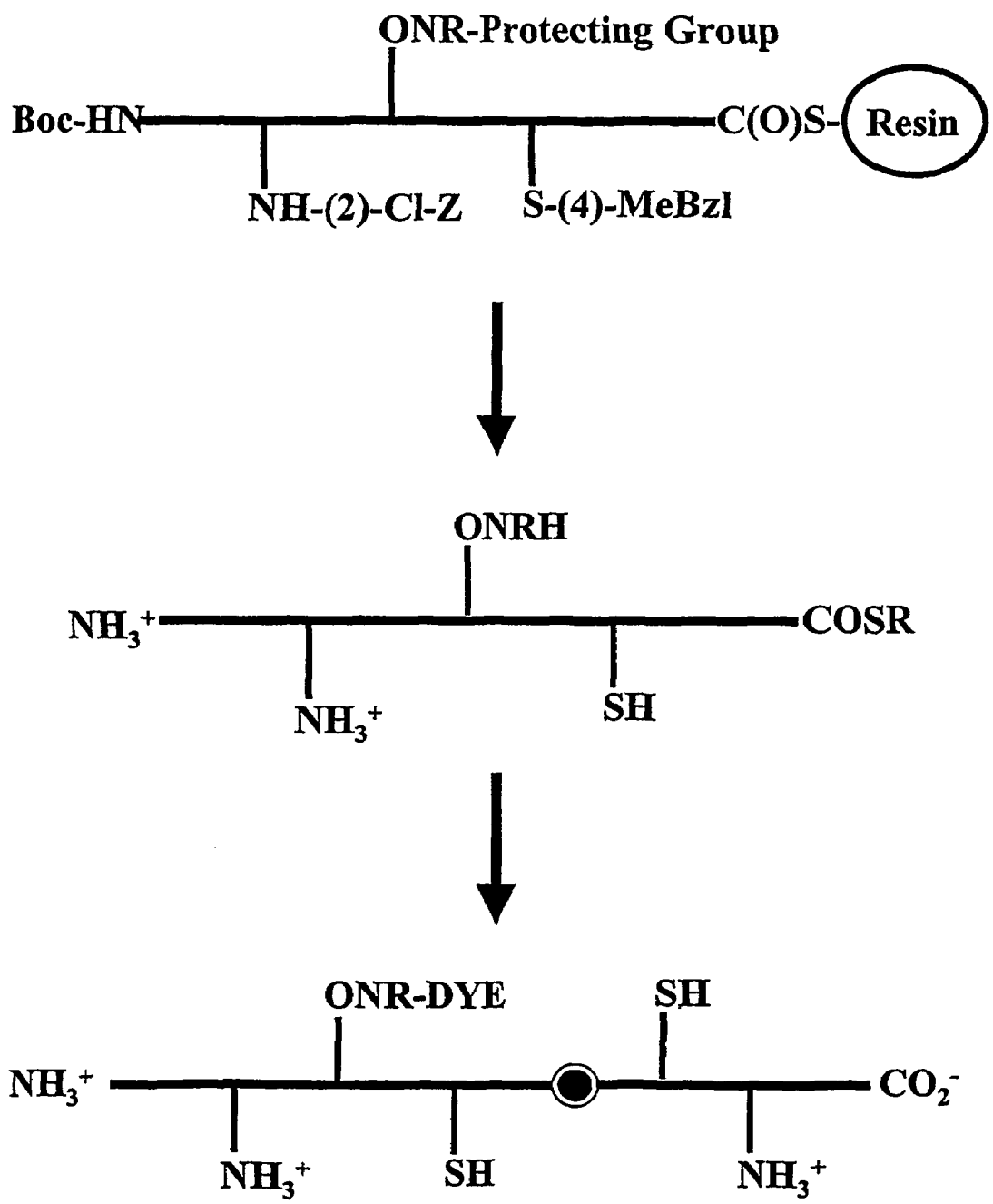
FIG. 1 illustrates a general strategy for site-specific labeling of polypeptides. The protected aminooxy group is incorporated during solid-phase peptide synthesis (synthesis on thioester-linker resin is shown); cleavage from the resin generates a peptide possessing unprotected sidechains, an aminooxy group and a C-terminal thioester, and ligation and subsequent site-specific labeling produces the full-length peptide with a functional molecule attached at the aminooxy nitrogen.

The following definitions are used, unless otherwise described: alkylene, alkenylene, alkynylene, etc. denote both straight and branched groups; but reference to an individual radical such as "propylene" embraces only the straight chain radical, a branched chain isomer such as "isopropylene" being specifically referred to. Aryl denotes a phenyl radical or an ortho-fused bicyclic carbocyclic radical having about nine to ten ring atoms in which at least one ring is aromatic.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methylalanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide). Other suitable amino and carboxy protecting groups are known to those skilled in the art (See for example, T. W. Greene, *Protecting Groups In Organic Sythesis*; Wiley: New York, 1981, and references cited therein).

The term "peptide" includes any sequence of 2 or more amino acids. The sequence may be linear or cyclic. For example, a cyclic peptide can be prepared or may result from the formation of disulfide bridges between two cysteine residues in a sequence. Thus, the term includes proteins, enzymes, antibodies, oligopeptides, and polypeptides. Peptide sequences specifically recited herein are written with the amino terminus on the left and the carboxy terminus on the right.

An "aminooxy group" is a group having the following formula

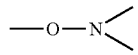

wherein the open valences are filled by any acceptable radical. A "secondary aminooxy group" is an aminooxy group where one of the open valences on the nitrogen is filled by a radical other than a hydrogen.

The term "functional molecule" includes any compound that can be linked to a peptide to provide a peptide conjugate having useful properties. Such conjugates may be useful for studying the structure or function of the peptide. Such conjugates may also be useful for drug screening, as pharmacological tools, as research tools, or as therapeutic agents. For example, the term functional molecule includes biophysical probes, peptides, polynucleotides, therapeutic agents, cross-linking groups (chemical or photochemical), a compound that modifies the biological activity of the peptide, or a caged molecule (e.g. a reporting molecule or a biologically active agent that is masked and that can be unmasked by photoactivation or chemical means).

The term "biophysical probe" includes any group that can be detected in vitro or in vivo, such as, for example, a fluorescent group, a phosphorescent group, a nucleic acid indicator, an ESR probe, another reporting group, a moiety, or a dye that is sensitive to pH change, ligand binding, or other enviornmental aspects.

Aminoacids and peptides that include one or more aminooxy groups are useful intermediates for preparing peptide conjugates. The aminooxy group(s) can typically be positioned at any suitable position on the aminoacid or peptide. For example, the aminooxy group(s) can conveniently be incorporated into the side chain of the amino acid or into one or more side chains of the peptide. Thus, as used herein with respect to the amino acids and peptides of the invention, the term "a radical comprising one or more aminooxy groups" includes any organic group that can be attached to the amino acid or peptide that includes one or more aminooxy groups. For example, the term includes a carbon chain having two to ten carbon atoms; which is optionally partially unsaturated (i.e. contains one or more double or triple bonds); which chain is optionally interrupted by one or more (e.g. 1, 2, or 3) —NH—, —O—, or —S—; which chain is optionally substituted on carbon with one or more (e.g. 1, 2, or 3) oxo (═O) groups; and which chain is optionally substituted with one or more (e.g. 1, 2, or 3) aminooxy groups. Preferably, the aminooxy group(s) are secondary aminooxy groups.

The term "cross-linking group" refers to any functionality that can form a bond with another functionality, such as photoaffinity label or a chemical crosslinking agent.

The term "caged molecule" includes a molecule or reporter group that is masked such that it can be activated (i.e. unmasked) at a given time or location of choice, for example using light or a chemical agent.

Specific and preferred values listed below for radicals, substituents, and ranges, are for illustration only; they do not exclude other defined values or other values within defined ranges for the radicals and substituents.

Specifically, $(C_1-C_6)$alkylene can be methylene, ethylene, propylene, isopropylene, butylene, iso-butylene, sec-butylene, pentylene, or hexylene; $(C_3-C_8)$cycloalkyl can be cyclopropyl, cyclobutyl, cyclopentyl, cyclohexyl, cycloheptyl, or cyclooctyl; $(C_2-C_6)$alkenylene can be vinylene, allylene, 1-propenylene, 2-propenylene, 1-butenylene, 2-butenylene, 3-butenylene, 1,-pentenylene, 2-pentenylene, 3-pentenylene, 4-pentenylene, 1-hexenylene, 2-hexenylene, 3-hexenylene, 4-hexenylene, or 5-hexenylene; $(C_2-C_6)$alkynylene can be ethynylene, 1-propynylene, 2-propynylene, 1-butynylene, 2-butynylene, 3-butynylene, 1-pentynylene, 2-pentynylene, 3-pentynylene, 4-pentynylene, 1-hexynylene, 2-hexynylene, 3-hexynylene, 4-hexynylene, or 5-hexynylene; and aryl can be phenyl, indenyl, or naphthyl;

A specific value for R is a radical of formula (V):

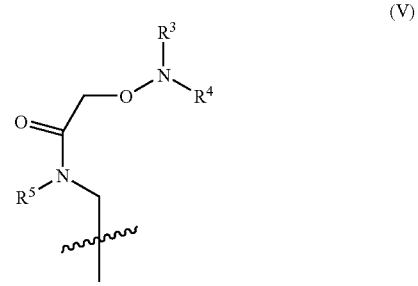

(V)

wherein
$R^3$ is hydrogen, $(C_1-C_6)$alkyl, an amino protecting group, or a radical comprising one or more aminooxy groups;
$R^4$ is hydrogen, or an amino protecting group; and
$R^5$ is hydrogen, or $(C_1-C_6)$alkyl.

A specific value for $R^1$ is hydrogen or benzyloxycarbonyl.
A specific value for $R^2$ is hydrogen.
A specific value for $R^3$ is methyl.
A specific value for $R^4$ is hydrogen, 2-chlorobenzyloxycarbonyl, or benzyloxycarbonyl.
A specific value for $R^5$ is hydrogen.
A specific value for $R^6$ is an antibody.
A specific value for $R^6$ is a peptide that includes about 2 to about 1000 amino acids. A more specific value for $R^6$ is a peptide that includes about 5 to about 500 amino acids. An even more specific value for $R^6$ is a peptide that includes about 10 to about 100 amino acids.

Specifically X is a linking group that is about 5 angstroms to about 100 angstroms in length. More specifically, X is a linking group of about 5 angstroms to about 25 angstroms in length.

Specifically X is —$R_a$—C(═O)—NH—$R_b$— wherein each of $R_a$ and $R_b$ is independently $(C_1-C_6)$alkylene. Preferably, each of $R_a$ and $R_b$-is methylene (—$CH_2$—).

A preferred value for $R^6$ is KKKEKERPEISLPSDFEHTI-HVGF DACTGEFTGMPEQWARLLQT (SEQ ID NO: 1)
A specific value for $R^7$ is hydrogen.
Another specific value for $R^7$ is $(C_1-C_6)$alkyl.
A preferred value for $R^7$ is methyl.

Specifcaly Y is a linking group that is about 5 angstroms to about 100 angstroms in length. More specifically, Y is a linking group of about 5 angstroms to about 25 angstroms in length.

A specific value for Y is $(C_1-C_6)$alkylene.
A preferred value for Y is methylene (—$CH_2$—).

Preferably, the biophysical probe can be an Alexa dye, a solvatochromic dye, an electrochromatic dye, or a dye that is sensitive to pH change, ligand binding, or other enviornmental aspects.

Preferred fluorescent groups include molecules that are capable of absorbing radiation at one wavelength and emitting radiation at a longer wavelength, such as, for example, Alexa-532, Hydroxycoumarin, Aminocoumarin, Methoxycoumarin, Amino methylcoumarin, Cascade Blue, Lucifer Yellow, NBD, P-Phycoerythrin, R-Phycoerthrin, (PE), PE-Cy5 conjugates, PE-Cy7 conjugates, Red 613, Fluorescein, BODIPY-FL, BODIPY TR, BODIPY TMR, Cy3, TRITC, X-Rhodamine, Lissamine Rhodamine B, PerCP, Texas Red, Cy5, Cy7, Allophycocyanin (APC), TruRed, APCy7 conjugates, Oregon Green, Tetramethylrhodamine, Dansyl, Indo-1, Fura-2, FM 143, DilC18(3), Carboxy-SNARF-1, NBD, Indo-1, Fluo-3, DCFH, DHR, SNARF, Monochlorobimane, and Calcein. More preferred fluorescent groups include rhodamine and Alexa-532.

Preferred nucleic acid indicators include intercolating agents and oligonucleotide strands, such as, for example, YOYO-1, Propidium Iodide, Hoechst 33342, DAPI, Hoerchst 33258, SYTOX Blue, Chromomycin A3, Mithramycin, SYTOX Green, SYTX Orange, Etkhidium Bromide, 7-AAD, Acridine Orange, TOTO-1, TO-PRO-1, Thiazole Orange, Propidium Iodide, TOTO-3, TO-PRO-3, LDS 751.

The synthetic intermediates (i.e. synthons) of the invention that include one or more aminooxy groups can be incorporated into peptides using a variety of techniques that are known in the art. For example, as discussed below, the synthons can be incorporated into a peptide using solid-phase peptide synthesis, solution-phase peptide synthesis, native chemical ligation, intein-mediated protein ligation, and chemical ligation.

Peptides may be prepared using solid-phase peptide synthesis (SPPS). For example, according to the SPPS technique, protected amino acids in organic solvents can be added one at a time to a resin-bound peptide chain, resulting in the assembly of a target peptide having a specific sequence in fully-protected, resin-bound form. The product peptide can then be released by deprotection and cleavage from the resin support (Wade, L. G., JR., Organic Chemistry 4th Ed. (1999)). As illustrated in Example 2 below, amino acids containing an aminooxy functional group can be incorporated into peptides using SPPS. Use of this methodology allows an amino acid containing an aminooxy functional group to be positioned at a desired location within a synthesized peptide chain.

Amino acids containing an aminooxy group can also be incorporated into a peptide using solution-phase peptide synthesis (Wade, L. G., JR. Organic Chemistry 4th Ed. (1999)). Solution-phase peptide synthesis involves protecting the amino-terminus of a peptide chain followed by activation of the carboxyl-terminus allowing the addition of an amino acid or a peptide chain to the carboxy-terminus (Wade, L. G., JR. Organic Chemistry 4th Ed. (1999)).

Native chemical ligation is a procedure that can be used to join two peptides together thereby producing a single peptide having a native backbone structure. Native chemical ligation is typically carried out by mixing a first peptide with a carboxy-terminal α-thioester and a second polypeptide with an amino-terminal cysteine (Dawson, P. E., et al., (1994), Science 266:776-779; Cotton, G. J., et al., (1999), J. Am. Chem. Soc. 121:1100-1101). The thioester of the first peptide undergoes nucleophilic attack by the side chain of the cysteine residue at the amino terminus of the second peptide. The initial thioester ligation product then undergoes a rapid intramolecular reaction because of the favorable geometric arrangement of the alpha-amino group of the second peptide. This yields a product with a native peptide bond at the ligation site. A polypeptide beginning with cysteine can be chemically synthesized or generated by intein vectors, proteolysis, or cellular processing of the initiating methionine. This method allows mixing and matching of chemically synthesized polypeptide segments. The synthons of the invention are particularly useful in combination with native chemical ligation, because native chemical ligation allows a synthetic peptide having a specifically positioned amino acid (e.g. a synthon of the invention) to be selectively ligated to another peptide. The ability to specifically incorporate aminooxy modified amino acids into a peptide chain allows useful moieties to be linked at any position within a peptide. Examples of such moieties that can be incorporated into a peptide using this method include, but are not limited to, phosphorylated or glycosylated amino acids, unnatural amino acids, tags, labels, crosslinking reagents, biosensors, reactive groups, and fluorophores. Another advantage of native chemical ligation is that it allows incorporation of peptides into a peptide that are unable to be added by ribosomal biosynthesis.

Intein-mediated protein ligation may also be used to selectively place amino acids containing aminooxy functional groups into peptides. Inteins are intervening sequences that are excised from precursor proteins by a self-catalytic mechanism and thereby expose reactive ends of a peptide. Intein vectors have been developed that not only allow single-step purification of proteins, but also yield polypeptides with reactive ends necessary for intein-mediated protein ligation (IPL) (also called expressed protein ligation)(EPL) (Perler, F. R. and Adam, E., (2000) Curr. Opin. Biotechnol. 11(4):377-83; and Evans, T. C., et al., (1998) Protein Sci 7:2256-2264). This method allows a peptide having a selectively placed amino acid containing an aminooxy functional group to be readily ligated to any peptide with reactive ends generated by intein excision.

Two peptides may also be linked through use of chemical ligation. Chemical ligation occurs when two peptide segments are each linked to functional groups that react with each other to form a covalent bond producing a non-peptide bond at the ligation site (Wilken, J. and Kent, S. B. H., (1998) Curr. Opin Biotechnol. 9:412-426). This method can be used to ligate a peptide having a specifically positioned aminooxy functional group to another peptide to produce a desired peptide that may be later linked to a detectable group.

A functional molecule ("D") can be attached to a peptide comprising an aminooxy group through a direct linkage (e.g. an amide bond O—N—C(═O)—D) or through a linking group. The structure of the linking group is not crucial, provided it does not interfere with the use of the resulting labeled peptide. Preferred linking groups include linkers that separate the aminooxy nitrogen and the detectable group by about 5 angstroms to about 100 angstroms. Other preferred linking groups separate the aminooxy nitrogen and the detectable group by about 5 angstroms to about 25 angstroms.

For example, the linking group can conveniently be linked to the detectable group through an: 1) amide (—N(H)C(═O)—, —C(═O)N(H)—), 2) ester (—OC(═O)—, —C(═O)O—), 3) ether (—O—), 4) thioether (—S—), 5) sulfinyl (—S(O)—), or 6) sulfonyl (—S(O)$_2$) linkage. Such a linkage can be formed from suitably functionalised starting materials using synthetic procedures that are known in the art.

The linking group can conveniently be linked to the nitrogen of the aminooxy group to form an amide (—O—

N(H)C(=O)— or a thiourea linkage (—O—N—C(=S)—N—) linkage, using reagents and conditions that are known in the art.

The aminooxy group can be attached to a peptide through a direct bond (e.g. a carbon-oxygen bond) between the aminooxy oxygen and a side chain of the peptide, or the aminooxy group can be attached to the peptide through a linking group. The structure of the linking group is not crucial, provided it does not interfere with the use of the resulting labeled peptide. Preferred linking groups include linking groups that separate the aminooxy oxygen and the side chain of the peptide by about 5 angstroms to about 100 angstroms. Other preferred linking groups separate the aminooxy oxygen and the side chain of the peptide by about 5 angstroms to about 25 angstroms.

A specific linking group (e.g. X or Y) can be a divalent ($C_1$-$C_6$)alkylene, ($C_2$-$C_6$)alkenylene, or ($C_2$-$C_6$)alkynylene chain, or a divalent ($C_3$-$C_8$)cycloalkyl, or aryl ring.

Thus, a simple and efficient synthetic methodology for site-specific labeling of peptides after synthesis has been developed that provides high yield, selectivity and compatibility with both solid-phase peptide synthesis and $C^\alpha$-thioester peptides. The approach and primary advantages can be summarized as follows:

(1) A protected aminooxy amino acid which can be incorporated into peptides has been synthesized;

(2) Procedures have been optimized to yield highly efficient and specific modification of the aminooxy nitrogen in the presence of unprotected competing nucleophiles, including cysteine, lysine and amino groups;

(3) One preferred electrophile that can be used for labeling, an activated carboxylic ester, is readily available in the majority of commercially available fluorescent dyes and labels;

(4) Labeling of the aminooxy group occurs after synthesis and purification, thus enabling the use of chemically sensitive fluorophores and labels that would otherwise not survive earlier synthetic procedures;

(5) The synthetic methodology is compatible with the steps required for the synthesis of proteins by total chemical synthesis or expressed protein ligation, namely synthesis of $C^\alpha$-peptide thioesters and amide-forming ligations; and (6) combinatorial screening of both the functional molecule and its placement will enable the rapid synthesis of optimally labeled polypeptide-based biosensors.

The invention will now be illustrated by the following non-limiting Examples.

EXAMPLE 1

Site-Specific Labeling of a Secondary Aminooxy Group

Under controlled pH conditions, the low pKa and enhanced nucleophilicity of an aminooxy group relative to other nucleophilic side chains found in peptides suggested the possibility of site-specific reaction with standard electrophiles such as succimidyl esters (FIG. 1). While selective labeling of a primary aminooxy group in the context of an unprotected peptide was achieved, extensive attemps to utilize the primary aminooxy group during synthesis failed. Even when protected as the 2-chlorobenzyloxycarbonyl carbamate, deprotonation of the primary aminooxy group allowed rapid acylation, so it could not be readily incorporated during peptide synthesis. Thus, under certain conditions, the use of a secondary aminooxy group may be preferred.

Figure 2:
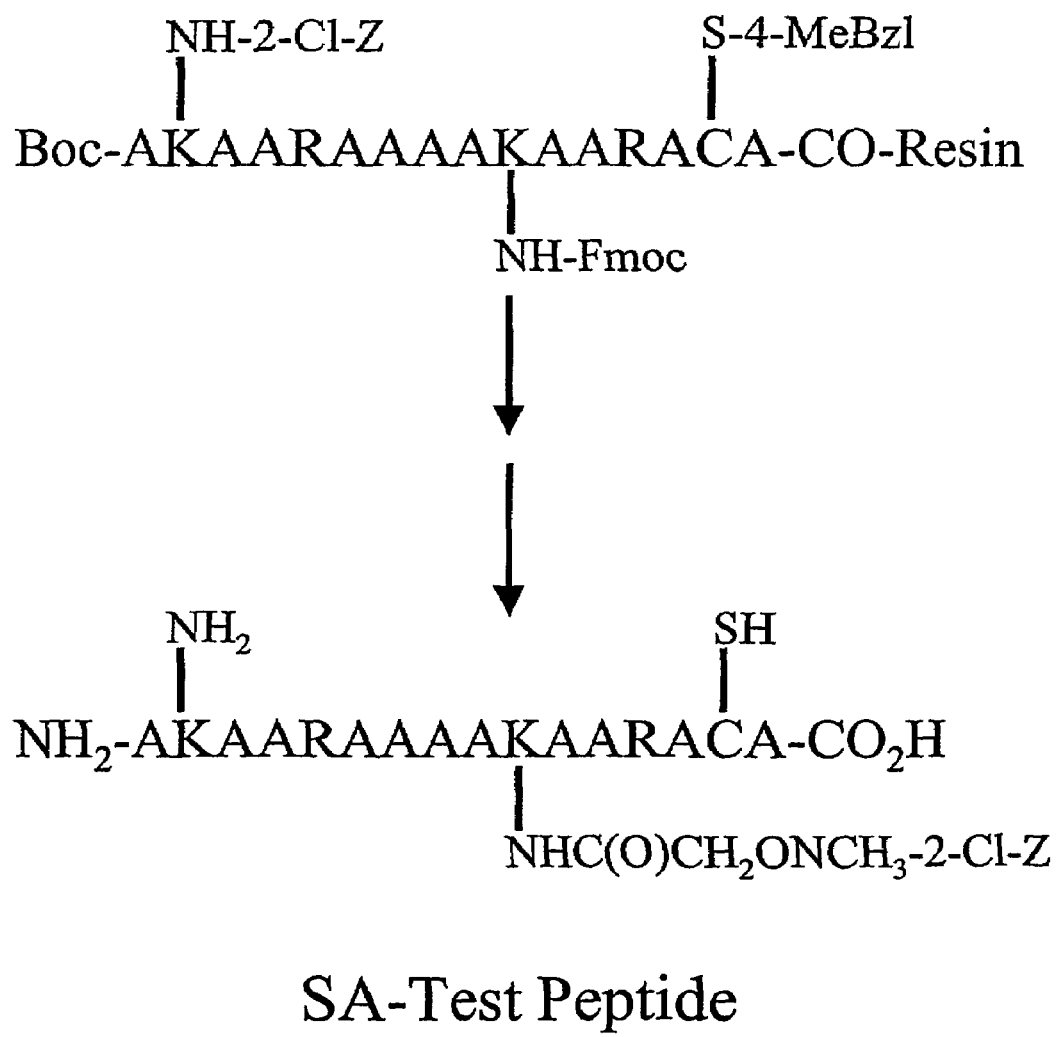
FIG. 2 illustrates the synthesis of PA-test and SA-test peptides.

A test peptide containing both a secondary aminooxy group and nucleophilic amino acids that were most likely to interfere with selective labeling at the aminooxy nitrogen (lysine, cysteine, and the amino-terminus) was prepared. As illustrated in FIG. 2, $NH_2$-AKAARAAAAK*AARACA-$C_2H$ (SEQ ID NO: 2), here designated SA-test peptide, was synthesized by incorporation and deprotection of N-(2-Cl-benzyloxycarbonyl)-N-methylaminooxy acetic acid (FIG. 4, 3) during solid phase peptide synthesis. The reactivity of the protected secondary aminooxy group was sufficiently attenuated to remain unreactive during Boc solid-phase peptide synthesis on thioester-linker resins. The 2-Cl-Z protection for the N-methylaminooxy amino acid was efficiently removed by standard HF cleavage procedures.

Conditions for selectively labeling the secondary aminooxy group were determined by varying the reaction pH and dye stoichiometry. Labeling with the succinimide ester of tetramethylrhodamine (TMR-OSu) was determined to be optimal in a solvent system consisting of 50% oDMSO/50% aqueous acetate buffer at pH of 4.7 with 2 equivalents of dye per mole of peptide (Table 1). The crude reaction products were separated from unreacted dye, and characterized by RP-HPLC and ESI-MS. Under these conditions, a single molecule of dye was incorporated on the aminooxy group with a 78% yield, based on HPLC quantification. However, side reaction products were also isolated and determined to be either SA-test peptide labeled with two dye molecules (~13%) or acetylated peptide products (~5%). The selectivity, as defined by the ratio of the peak areas of desired single-labeled product over double-labeled products, was 6/1 (Table 1).

TABLE 1

Labeling of SA-Test Peptide

| Buffers | | | | Dye | Percentage | | | |
|---|---|---|---|---|---|---|---|---|
| Reaction | Gel Filtration | TCEP | pH* | Equivalents | SM | 1Dye | 2Dye | Selectivity |
| Acetate | $(NH_4)HCO_3$ | No | 4.7 | 1.0 | 32 | 56 | 7 | 8:1 |
| Acetate | $(NH_4)HCO_3$ | No | 4.7 | 1.5 | 14 | 63 | 13 | 4.5:1 |
| Acetate | $(NH_4)HCO_3$ | No | 4.7 | 2.0 | 0 | 78 | 13 | 6:1 |
| Acetate | $(NH_4)HCO_3$ | No | 4.7 | 2.4 | 0 | 76 | 17 | 4.5:1 |
| Acetate | $(NH_4)HCO_3$ | No | 4.7 | 3.0 | 0 | 71 | 23 | 3:1 |
| Citrate | 0.1% TFA | Yes | 4.7 | 4.3 | 4.3 | 89.6 | 4.1 | 22:1 |
| Carbonate | 0.1% TGA | Yes | 9.0 | 0.99 | 13 | 85 | 0 | 51:1** |

It was determined that many of the side reactions occurred during size exclusion chromatography in the ammonium bicarbonate solvent used to separate reaction products. Using an acidic solvent system, 0.1% TFA, virtually eliminated multiply labeled side products leading to considerable improvements in both selectivity and yield. Including a mild reducing agent, tris(2-carboxyethyl)phosphine CTCEP), in the reaction buffer also significantly curtailed several minor side reactions revealed by HPLC, especially disulfide formation. Labeling and gel filtration under these optimized conditions produced a 70% recovered yield of labeled SA-test peptide (90% yield based on HPLC quantitation), 90% of which was labeled with only a single dye at the aminooxy amine. The labeling selectivity was increased to 22/1 (Table 1).

Figure 3:
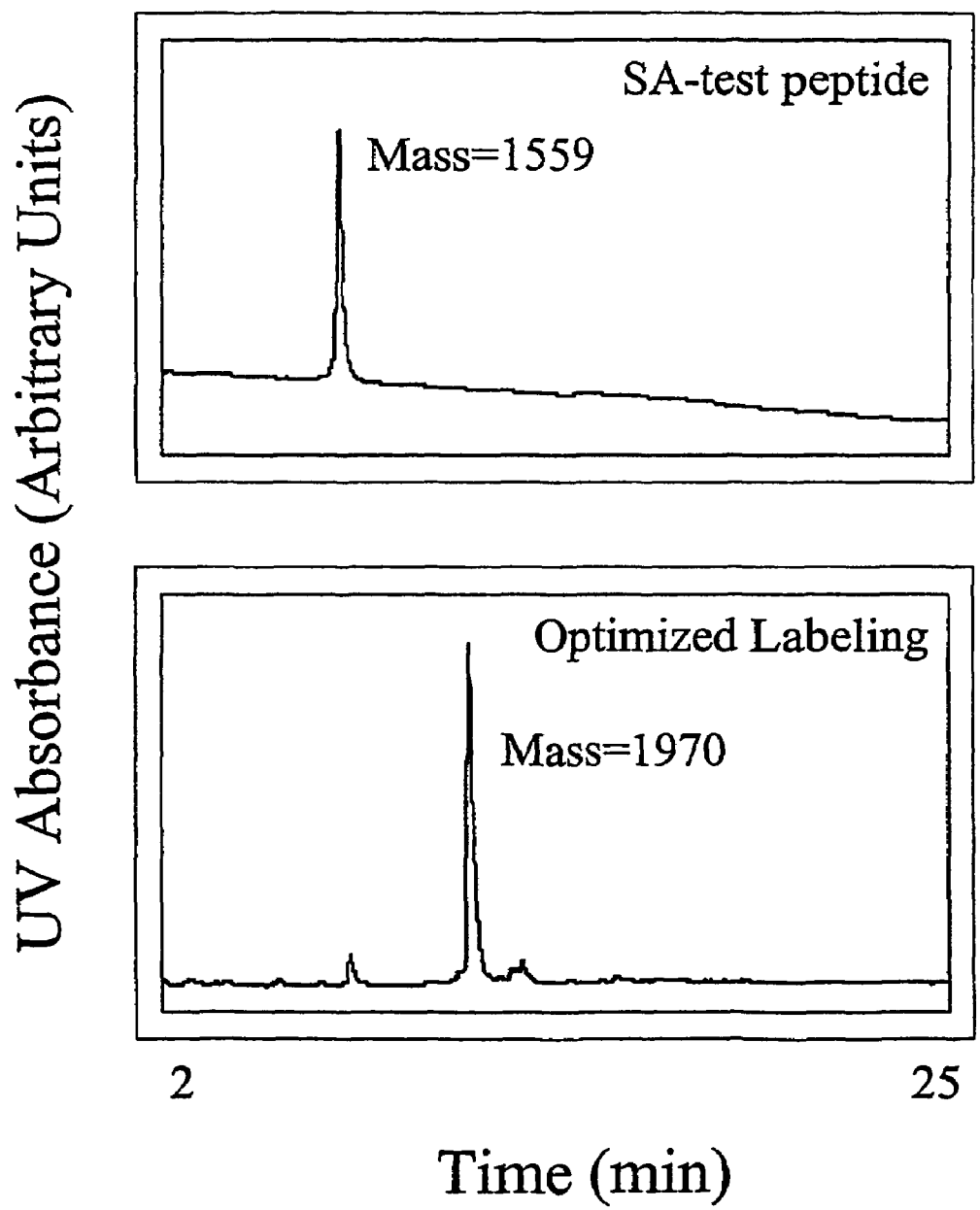
FIG. 3 shows HPLC analysis of purified SA-test peptide (top) and crude reaction products from optimized labeling conditions (bottom).

The purity of the product was confirmed using RP-HPLC, mass spectroscopy, further chemical reaction, and isolation of purposefully overlabeled products. The labeled peptide eluted as a single peak under all HPLC conditions tested with a mass consistent with that predicted for singly-labeled SA-test peptide (Mass=1970). To determine that the labeling site was indeed at the N-methylaminooxy group, a selective zinc/acetic acid reduction procedure was used to cleave the N—O bond (FIG. 3). HPLC of the reduction reaction showed >98% conversion of the starting material and a new earlier eluting peak. The mass of this peak (1530 amu) corresponded to the predicted mass of the unlabeled SA-test peptide cleaved at the aminooxy N—O bond. The residual zinc was washed several times with a saturated solution of EDTA in water, which demonstrated that the reduction reaction was complete.

To eliminate the unlikely possibility that the HPLC peak containing isolated single-labeled SA-test peptide product was a mixture of two labeled species, SA-test peptide was reacted under higher pH conditions (pH 9.0) to label all reactive sites. SA-test peptide contained 3 nucleophilic labeling sites which would be irreversibly labeled: aminooxy, lysine, and N-terminal amine. Dye labeling at high pH generated a mixture of peptides labeled at all possible combinations of sites with 1, 2 or 3 dyes. HPLC analysis of this reaction mixture showed 8 peaks, indicated by ESI-MS to correspond to unreacted SA-test peptide, SA-test peptide single-labeled at the aminooxy nitrogen, and six additional peaks corresponding to two single-labeled peptides, three peptides bearing two dyes and a single triply-labeled peptide species. This experiment revealed the HPLC retention times of all these products, none of which coeluted with the peak identified as SA-test peptide labeled with a single dye on the secondary aminooxy nitrogen.

Site-specific labeling of the aminooxy group could even be achieved at basic pH (Table 1). Using pH 9.0 carbonate buffer in our solvent system, addition of 0.5 equivalents of dye produced, after 3 hours, ~50% conversion of the starting SA-test peptide to a single peak with the elution time of the desired singly-labeled product. After addition of another. 0.5 equivalents of TMR-OSu and an additional 3 hours of reaction time, HPLC showed ~85% conversion to a peak with the retention time of the desired product Two minor peaks (~2-3% of total peak area), were also apparent and corresponded to the two other single-labeled SA-test peptide species identified in the multiple labeling experiment above. The N-hydroxysuccinimide ester of rhodamine clearly showed selective reactivity with the aminooxy group.

The selectivity observed at higher pH cannot be explained by the nucleophicity of the aminooxy group alone. In fact, others have shown that at, in an an uncatalyzed reaction with phenyl acetate at high pH, amines are more reactive than O-alkylaminooxy groups. Therefore we suggest that kinetic factors are contributing to the selective reactivity of the N-methylaminooxy group, even when competing groups are not protonated. Possible reasons for this include: (1) the aminooxy oxygen localizes the nitrogen near the activated ester via formation of a hydrogen bonded "bridged" intermediate (2) a base catalyzed reaction pathway under the conditions of our reaction. This exceptional reactivity has important practical implications, as it can allow the selective labeling of acid-labile polypeptides and synthetic proteins under physiological or basic conditions.

EXAMPLE 2

The Secondary Aminooxy Group is Compatible with C-Thioesters and Amide-Forming Ligation Preparation of Proteins by Total Chemical Synthesis Often Requires the ligation of large polypeptides prepared by solid-phase peptide synthesis on thioester-linker resins. The most generally applicable methods available for ligations are native chemical ligation and expressed protein ligation. These processes utilize the same basic chemistry to join two peptides, one with an N-terminal cysteine and the other with a C-terminal thioester, through a regiospecific and site-specific reaction to generate a larger polypeptide. The application of aminooxy-labeling chemistry to the synthesis of large polypeptides and proteins requires compatibility with these solid-phase peptide synthesis and ligation chemistries.

Figure 4:
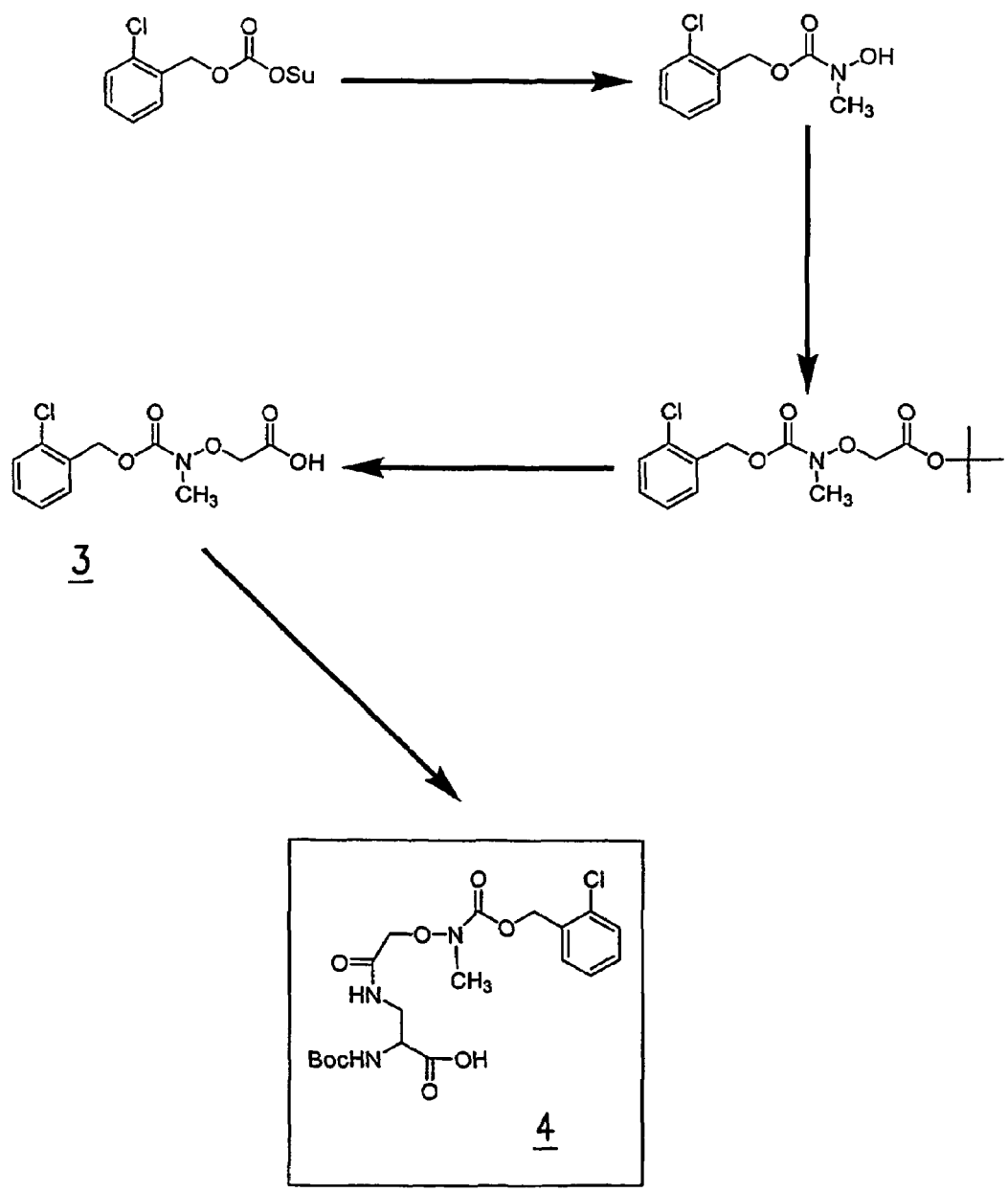
FIG. 4 illustrates the synthesis of a protected intermediate of the invention (4).

The optimal approach for utilizing aminooxy-labeling chemistry in the chemical synthesis of proteins is direct incorporation of the aminooxy group as part of an amino acid used during standard solid-phase peptide synthesis. For this purpose, we generated a suitably protected N-methylaminooxy amino acid, α-Boc-β—[N—(2 Chlorobenzyloxycarbonyl)-N-Methylaminooxy Acetyl]-α,β-Diaminopropionic Acid [Boc-2-Cl-Z(SA)Dapa-OH] (4), as shown in FIG. 4. This amino acid, referred to as SAOD, was incorporated into the peptide sequence LY-(SAOD)-AG-MPAL thioester by synthesis on TAMPAL thioester-linker resin, as described below in the Methods. (MPAL is the C-terminal mercaptopropionyl-leucine group generated by cleavage of a peptide from TAMPAL resin, see Hojo, H., et al., *Bull. Chem. Soc. Jpn.* 1993, 66:2700-2706; and Hackeng, T. M. et al., *Proc. Natl. Acad. Sci. USA*. In press)

Ligation of the LY-(SAOD)-AG-MPAL (SEQ ID NO: 3) thioester peptide with the peptide CRANK-NH$_2$ (SEQ ID NO: 4), was tested using standard procedures employing phosphate buffer with 6M guanidine hydrochloride at neutral pH in the presence of 2-3% thiophenol by volume. The ligation proceeded over 24 hours and generated the desired ligation product, LY-(SAOD)-AGCRANK-NH$_2$ (SEQ ID NO: 5), at ~85% yield. The major side product was attributable to modification of unligated CRANK-NH$_2$ peptide under the ligation conditions (mass=714.5, data not shown), and was not related to the presence of the aminooxy group. There was also a single time-dependent side reaction, which generated a product of 14 mass units lower than the desired. Using high concentrations of reacting peptides and isolating the ligation product after 24 hours reduced this side reaction to acceptable levels (<5%).

The ligation of a peptide containing multiple potentially reactive functional groups, including a hexahistidine tag useful for affinity chromatography was also tested. Coupling CEYRIDRVRLFVDKLDNIAQVPRVGAA-HHHHHH (SEQ ID NO: 6) to LY-(SAOD)-AG-MPAL thioester proceeded to completion in 5 hours with minimal side reactions. In both ligation reactions, there was less than 1% LY-(SAOD)-AG-MPAL self condensation product, indicating that the aminooxy group and thioester do not appreciably react with one another under the ligation conditions. These results demonstrate that the inclusion of an unprotected aminooxy group in the peptide chain is compatible with native chemical ligation.

Labeling of the two ligation products using tetramethylrhodamine succinimide ester proceeded with selectivity similar to that for the SA-test peptide. HPLC integration indicated that the product of the LY-(SAOD)-AG-MPAL ligation with CRANK-NH$_2$ was labeled with greater that 95% efficiency and with a selectivity of 34:1. Mass spectral analysis and zinc reduction demonstrated labeling at only the aminooxy group. For the longer hexahistidine-containing polypeptide ligation product, selectivity for the aminooxy group was greater than 10:1, but it was difficult to achieve high yields. The histidines could potentially have been affecting yield and selectivity by catalyzing nucleophilic attack on the succinimide ester of the reactive dye. Inclusion of guanidine hydrochloride in the reaction solvent increased the yield to approximately 50%, indicating that folding or poor solubility of the peptide was a factor in preventing access of the reactive dye to the aminooxy group. Selectivity was also improved, presumably because of the availability of the reactive secondary aminooxy group. Single-site labeling at the aminooxy group was proven by mass spectral analysis of trypsin and α-chymotrypsin digests of the labeled polypeptide product.

EXAMPLE 3

Specificity of Labeling in Protein Domains Containing Aminooxy Amino Acids

As a control to establish the selectivity of labeling for aminooxy amino acid, the labeling of native β-Lactoglobulin with tetramethylrhodamine N-hydroxysuccinimide ester was attempted. It was found that non-specific labeling of this 162 aa protein containing 15 lysines and 4 cysteines was minimal (<1%) even after 6 hours.

Finally, the GTPase binding domain of p21 activated kinase (45 aa, 4 lys, 1 cys) with a secondary aminooxy amino acid incorporated at the amino-terminus (SAOD-PBD) was prepared. Previous experiments have demonstrated that PBD domains labeled with fluorescent reporter dyes at this terminus could be used as biosensors of GTPase activation. Labeling of PBD using the new methodology would enable the production of sufficient quantities to apply the biosensors in vivo and in pharmaceutical screening applications, and would allow incorporation of sensitive detectable groups enabling applications within living cells.

SAOD-PBD was readily labeled with Alexa-532 N-hydroxy-succinimide ester by titration addition of dye at pH 4.7 over 72 hours. The labeling efficiency was commensurate with that reported for the longest model peptide (~50% yield by HPLC quantitation) and there was no indication of multiple labeling. In this case, isolation of labeled SAOD-PBD by RP-HPLC proved difficull Separation to baseline resolution was not achieved, but small quantities of unlabelled PBD in the labeled product do not preclude the use of the labeled material in biosensor applications. Previous reports indicate that separation of labeled product from starting polypeptide is highly dependent on the specific peptide and the attached dye.

These results demonstrate that the optimized site-specific labeling chemistry reported here is compatible with the steps required for the preparation of proteins by total chemical synthesis.

EXAMPLE 4

Materials and Methods

General: For column chromatography, silica gel (230-400 mesh) was used in standard glass columns with gravity or air pressure. Reversed-phase high performance liquid chromatography (RP-HPLC) was performed on a Waters HPLC system with UV detection at 214 nm using either a Vydac C-18 analytical column (5 µm, 0.46×25 cm), a Waters RCM 8×10 module equipped with a semipreperative Delta Pack C-18 Radial Pack cartridge column (15 µm, 8×100 mm) from Millipore, or a Vydac C-18 preparative scale column (15 µm, 1.0×25 cm). Linear gradients of solvent B (0.09% TFA in 90% acetonitrile/10% water) in solvent A (0.1% TFA in water) were used for all HPLC chromatographic separations.

Mass spectra of peptides were obtained either with a Sciex API-I electrospray ionization (ESI) triple-quadruple mass spectrometer (PE Biosystems, Foster City), or matrix assisted laser desorption ionization time-of-flight (MALDI-TOF) instruments from Thermo Bioanalysis (Ihermo Bioanalysis, LTD., UK) or Kratos Analytical (Chestnut Ridge, N.Y.). For ESI-MS, the observed masses reported were derived from the experimental m/z states for all observed charge states of a molecularspecies using the program MacSpec (Sciex, version 2.4.1) for electrospray mass spectrometry. MALDI-MS observed masses were relative to internal calibration using α-cyano-hydroxycinnammic acid or sinipinic acid matrices. Calculated masses reported were derived from either MacProMass (Terry Lee and Sunil Vemuri, Beckman Research Institute, Duarte, Calif.) or PAWS (Version 8.1.1, ProteoMetrics) and reflect the average isotope composition of the singly-charged molecular ion. Proton nuclear magnetic resonance spectrometry was recorded on a Bruker AC-250 mass spectrometer and data was analyzed using WinNMR (Bruker Instruments). Ultraviolet-Visible spectroscopy was performed on a Hewlett-Packard photodiode-array spectrophotometer.

Boc-L-amino acids were purchased form Novabiochem (La Jolla, Calif.) or Bachem Bioscience, Inc. (King of Prussia, Pa.). [[4 (Hydroxymethyl)phenyl]-acetamido]methyl (—OCH$_2$-Pam) Resin was purchased from PE Biosystems (Foster City, Calif.) and methylbenzhydrylamine (MBHA) resin was purchased from Peninsula Laboratories, Inc. (San Carlos, Calif.). Solvents were Synthesis grade or better and were purchased from Fisher Scientific (Tustin, Calif.). Trifluoroacetic acid (TFA) and anhydrous hydrogen fluoride were purchased from Halocarbon (New Jersey) and Matheson Gas (Rancho Cucamonga, Calif.). Dyes were obtained from Molecular Probes (Eugene, Oreg.). All other reagents were analytical grade or better and were purchased from Aldrich (Milwaukee, Wis.), Lancaster (Windham, N.H.), Peptides International (Louisville, Ky.) or Richelieu Biotechnologies (Montreal, Canada).

Peptide Segment Synthesis. Synthesis of peptides was carried out manually using optimized stepwise solid-phase synthesis methods with in situ neutralization and HBTU activation procedures for Boc chemistry on either —OCH$_2$-Parn, MBHA, or Trt-protected mercaptopropionyl-Leu (TAMPAL) resin (Hojo, H., et al., *BulL Chem. Soc. Jpn.*

1993, 66:2700-2706; Hackeng, T. M.et al., *Proc. Natl. Acad Sci. USA*. In press; and Schnolzer, M., et al., *Int. J. Peptide Protein Res*. 1992, 40:180-193). Standard Boc protecting group strategies were employed. Coupling was monitored by quantitative ninhydrin assay after 15 minute coupling cycles. After chain assembly, standard deprotection and cleavage from the resin support was carried out by treatment at 0° C. for 1 hour with anhydrous HF containing either 10% p-cresol or anisole as scavenger. Purification was performed using RP-HPLC. Synthesis of TAMPAL Resin (Hojo, H., et al., *Bull. Chem. Soc. Jpn.* 1993, 66:2700-2706). 2.5 grams of MBHA resin (0.865 mmol/g, 2.16 mmol of amine) was swelled in DMF. Boc-Leu-OH (1.1 grams, 4.4 mmol) was activated with HBTU (8 ml, 0.5M solution) and DIEA (2 ml), then coupled to the MBHA resin until complete reaction by ninhydrin assay. The $N^\alpha$-Boc group of the linked leucine was removed with neat TFA, then S-Trt-β-mercaptopropionic acid (1.5 grams, 4.3 mmol), activated in the same manner as Boc-Leu-OH, was added to the deprotected Leu-MBHA resin and allowed to couple until complete reaction. The S-Trt-β-mercaptopropionyl-Leu-MBHA resin was washed extensively with DMF, then DCMIMeOH (1/1), and finally dried in vacuo to yield 3.39 grams of thioester resin. Substitution calculated by weight gain yielded 0.549 mmol/gram.

Deprotection of TAMPAL Resin: S-trityl protection was removed by two 5 minute treatments with 95% TFA/5% triisopropylsilane. The deprotected resin was extensively with DMF before coupling the first amino acid, activated using optimized in situ neutralization protocols.

Synthesis of N-(2-Cl-benzyloxycarbonyl)-N-Methylhydroxylamine (1) (Jencks, W. P., Carriuolo, J. *J. Am. Chem. Soc.* 1960, 82:675; Jencks, W. P. *J. Am. Chem. Soc.* 1958, 80:4581, 4585). N-methylhydroxylamine hydrochloride (0.95 g, 11.37 mmol) was dissolved in 3 ml of water with rapid stirring. The pH of this solution was adjusted to 6-7 by dropwise addition of a saturated solution of sodium bicarbonate. 2° Chlorobenzyloxycarbonyl-N-hydroxysuccinimidyl carbonate (1.2 g, 4.23 mmol) was dissolved in 4 ml of THF and added slowly to the rapidly stirring solution of neutralized N-methylhydroxylamine. After stining at room temperature for 14 hours, the reaction was quenched with 20 ml of saturated sodium bicarbonate and extracted three times with 20 ml ethyl acetate. The combined ethyl acetate layers were washed once with saturated sodium bicarbonate, dried over anhydrous sodium sulfate and the solvent was removed in vacuo to yield 0.77 g (3.77 mmol, 84%) of an off-white solid. TLC Rf=0.2 (Hex/EtOAc/AcOH 80/20/1). $^1$H NMR: 3.23 (s, 3H), 5.25 (s, 2I), 7.24 (m, 2H), 7.37 (m, 2H). HRMS: Expected=216.0427, Observed=216.0425.

Synthesis of N-(2-Cl-benzyloxycarbonyl)-N-Methylaminooxy Acetic Acid-Tert-butyl ester (2) (Jerry March in Advanced Organic Chemistry, Third Edition. John Wiley & Sons, New York. 1989, pp 381; and Nyberg, D. D., Christensen, B. E. *J. Am. Chem. Soc.* 1957, 79:1222; Motorina, I. A., et al., *Synlett* 1996, 389). Compound 1 (0.96 g, 4.71 mmol) was dissolved at room temperature in 10 ml of THF with rapid stirring. Bromoacetate tert-butyl ester (1.05 g, 5.38 mmol) was added, then sodium iodide (1.5 g, 10.01 mmol) followed by DIEA (2.5 ml, 15.92 mmol). The reaction changed to an orange-yellow color after addition of sodium iodide. The reaction was quenched with 30 ml water after complete reaction (~3 hours) and extracted 3 times with ethyl acetate. The combined ethyl acetate layers were dried over sodium sulfate and the ethyl acetate was removed in vacuo. The resultant oily solid was purified by silica chromatography on 230-400 mesh silica gel using hexanes/ethyl acetatelacetic acid (80/20/1) to yield 1.40 g (4.29 mmol, 90%) of a pure yellow oil. TLC Rf=0.5 (Hex/EtOAc/AcOH 80/20/1). $^1$H NMR: 1.46 (s, 9H), 3.29 (s, 3H), 4.36 (s, 2H), 5.26 (s, 2H), 7.24 (m, 2H), 7.40 (m, 2H). HRMS: Expected Mass=330.1108, Observed Mass=330.1104.

Synthesis of N-(2-Cl-benzyloxycarbonyl)-N-Methylaminooxy Acetic Acid (3) (Bryan, D. B., et al, *J. Am. Chem. Soc.* 1977, 99:2353). Compound 2 (1.1 g, 3.30 mmol) was dissolved into 4 ml of DCM and, with rapid stirring, neat TFA (5 ml) was added dropwise over 2 minutes at room temprature. After 1 hour, the reaction was quenched with 20 ml water, extracted 3 times with DCM, and the combined DCM layers were dried over sodium sulfate. The DCM was removed in vacuo to yield 0.9 g (30.2$^8$ mmol, 99%) of an off-white solid. TLC Rf=0.2 (Hex/EtOAc/AcOH 80120/1). $^1$H NMR: 3.23 (s, 3H), 4.50 (s, 2H), 5.32 (s, 2H), 728 (m, 2H), 7.40 (m, 21H). HRMS: Expected Mass=274.0482, Observed Mass=274.0479.

Synthesis of N-(2-Cl-benzyl xycarbonyl)-N-Methylaminooxyacetyl-α-Boc-α,β-Diaminopropionic Acid [(SA) Dapa-OH](4) (Wahl, F., Mutter, M. *Tett. Lett.* 1996, 37:6861-6864; and Anderson, G. W., et al., *J. Am. Chem. Soc.* 1964, 86:1839). N-(2-Chlorobenzyloxycarbonyl)-N-Methylaminooxy Acetic Acid (3) (2.5 g, 9.2 mmol) was activated with N-hydroxysuccinimide (2.11 g, 2 equiv.) and DIC (1.440 ml, 1.0 equiv.) in 20 ml DCM. This reaction was rapidly stirred at room temperature for 2 hours prior to the addition of $N^\alpha$-Boc-α,β-diaminopropionic acid (2.3 g, 1.2 equiv.) and DIEA (3.20 ml, 2 equiv.). After 4 hours, the DCM solvent was removed in vacuo, and 50 ml ethyl acetate was added. The ethyl acetate layer was washed twice with 0.5M acetate buffer, pH=4.0, then twice with 0.1N sulfuric acid. The combined acid washes were then washed with 50 ml ethyl acetate. The combined ethyl acetate layers were dried over sodium sulfate, then concentrated in vacuo to yield a viscous yellow oily solid. This solid was subjected to 3 hexane precipitations from diethyl ether to yield 2.16 g (51% yield) of an off-white solid. TLC Rf=0.2-0.4 (Hex/EtOAc/AcOH 30/70/0.5). $^1$H NMR: 1.45 (s, 9H), 3.16 (s, 3H), 3.54 (d-of-t, 1H, J=14.3, 4.6 Hz), 3.93 (m, 1H, J=14.3, 7.5, 4.6 Hz), 4.31 (s, 0.5H), 4.38 (s, 1H), 4.45 (s, 1H), 4.51 (s, 0.5H), 5.34 (s, 2H), 5.97 (broad-d, 1H, J=7.3 Hz), 7.30 (m, 2H), 7.43 (m, 2H), 8.50 (broad-s, 1H). HRMS: Expected Mass=460.1487, Observed Mass=460.1480.

Synthesis of Secondary Aminooxy Test Peptide (SA-test peptide). The SA-test peptide, NHrAIKAARAAAAK*RACA-CO$_2$K, was synthesized with Lys 10 side chain Fmoc protection as described previously (Canne, L. E., et al., *J. Am. Chem. Soc.* 1995, 117:2998-3007). Incorporation of the secondary aminooxy group was accomplished by coupling 2-Cl-Z protected N-methylaminooxyacetic (300 mgs, 1.09 mmol) activated with Diisopropylcarbodiimide (157 ul, 1.00 mmol) and N-hydroxysuccinimide (140 mgs, 1.22 mmol) in 2 ml DCM for 1-2 hours, then diluted with 2 ml DMF just prior to coupling to the ε-amino group of Lys 10. Optimized coupling, cleavage and purification protocols were utilized. Amino acid analysis was consistent with the desired peptide. Expected Mass=1560, Observed Mass=1559.

Synthesis of LY-(SAOD)-AG-MPAL-Thioester. LY-(SAOD)-AG-MPAL-Thioester was synthesized using optimized in situ neutralization protocols for Boc chemistry on TAMPAL resin. Coupling of the $N^\alpha$-Boc-(SA)Dapa-OH amino acid was accomplished by reacting the in situ activated N-hydroxysuccinimide ester to the deprotected amino-terminal nitrogen of alanine (Canne, L. E., et al., *J. Am. Chem. Soc.* 1995, 117:2998-3007). (SA)Dapa-OH (4) (230 mgs, 0.5 mmol) was dissolved in 1 ml DCM and N-hydroxysuccinimide (115.1 mgs, 1.0 mmol) and DIC (74.4 µl, 0.47 mmol) were added. The reaction was mixed briefly and allowed to activate for 1-2 hours at room temperature prior to coupling to the deprotected N-terminus of the peptide chain. After this coupling, no further modifications of the synthetic protocols were required. Expected mass=797, Observed mass=797.

Ligation of LY-(SAOD)-AG-MPAL-Thioester with CRANK-NH$_2$ Peptide. LY—(SAOD)-AG-MPAL-Thioester (3 mg, 3.8 µmol) was dissolved into 100 ul of 50 mM phosphate buffer containing 6M guanidine hydrochloride, pH=7.2. To this solution was added CRANK-NH$_2$ peptide dissolved into 100 µl of the same phosphate buffer and 3 ul of thiophenol. The reaction was monitored by analytical reversed-phase HPLC. After 24 hours, the ligated product, LY-(SAOD)-AGCRANK-NH$_2$ (SEQ ID NO: 10), was isolated by semi-preparative reversed-phase HPLC (gradient=10-50% B over 60 minutes) and lyophilized to yield a fluffy white solid. Amino acid analysis was consistent with the desired product peptide. Expected Mass=1168, Observed Mass=1168.

Ligation of LY-(SAOD)-AG-MPAL-Thioester with CEYRIDRVRLFVDKLDNIAQ-VPRVGAA-HHHHHH (SEQ ID NO: 7). LY—(SAOD)-AG-MPAL (0.3 mgs, 0.37 mmol) and CEYRIDR-VRLPFVDKLCNIAQ-VPRVGAA-HHH-HHH (1.5 mgs, 3.8 mmol) were subjected to the same ligation and purification conditions as described above to yield 1.0 mgs (58% yield) of a white fluffy solid. Expected Mass=4518, Observed Mass=4517.

Synthesis of Amino-Terminal P21 Binding Domain (PBD) Peptide Fragment, (SAOD)-KKKEKERPEISLPSDFE-HIVGFDA-MPAL Thioester (SEQ ID NO: 8): Secondary aminooxy containing amino-terminal PBD thioester were synthesized as described above using TAMPAL resin. HF cleavage utilizing p-Cresol scavenger followed by HPLC purification yielded (SAOD)-KKKPEKERPEISLPSDFE-HITHIVGFDA-MPAL containing two DNP groups protecting the histidines. Mass Expected=3745, Mass Observed=3745.

Synthesis of Carboxy-Terminal of P21 Binding Domain (PBD) Peptide Fragment, CTGEFTGMPEQWARLLQT (SEQ ID NO: 9): The native carboxy-terminal half of PBD was synthesized using standard FMOC synthesis protocols by the Scripps Peptide and Protein Core Facility. Mass Expected=2068, Mass Observed=2068.

Synthesis of SAOD-Modified PBD, SAOD-KEKERPEIS-LPSDFEHIVGFDA-CTGEFTGMPEQWARLLQT (SEQ ID NO: 11): 1.5 mg of SAOD-KKKEISLPSDFEHTHVG-FDA-MPAL (0.4 mmol) was ligated to 1 mg (4.8 mmol) of carboxy-terminal fragment, CTGEF=GMPEQWARLLQT, as described above. After 48 hours, the ligated PBD proteins were isolated by RP-HPLC and lyophilized, 1.5 mg (70% yield), Mass Expected=5262, Mass Observed=5262.

Selective Labeling of SA-Test Peptide with Tetramethylrhodamine N-hydroxysuccinimidyl ester. A solution of SA-test peptide (3.396 µg/µl, 2.18 mM) in 5% acetate buffer, pH=4.7 incorporating 5 mM TCEP was utilized for labeling. A stock solution of dye (5 µg/µl, 9.5 mM) was made by dissolving TMR-OSu in neat DMSO. For each reaction, the dye stock was diluted so that the desired number of dye equivalents could be added in 20 µl of DMSO. The following equivalents of dye were tested: 1.2, 1.5, 1.8, 2.0, 2.4, 3.0, and 4.3. With constant stirring, 20 µl of dye solution was added in two 10 µl aliquots to 20 µl of peptide solution at room temperature. The second aliquot of dye in DMSO was added 10 minutes after the initial dye addition. After complete addition of dye, the reaction was briefly vortexed, then incubated at room temperature. After 3 hours, the labeled reaction product(s) were separated from unreacted dye by gel filtration on Sephadex G-10 or G-15 columns using either 100 µM ammonium bicarbonate or, after optimization, 0.1% TFA in water. The individual peptide product(s) were then separated by RP-HPLC and analyzed by ESI MS. Mass Expected=1971, Mass Observed=1970.

Non-Selective Labeling of SA-Test Peptide with Tetramethylrhodamine N-hydroxysuccimide ester. SA-test peptide (3.396 µg/µl, 2.18 mM) was dissolved 100 mM sodium carbonate, pH=9.01 containing 5 mM TCEP. 18 µl of neat DMSO was added to 20 µl of peptide solution. With rapid mixing, 1 µl stock dye solution in DMSO was added to this mixture. Upon completion of addition, the reaction was vortexed briefly, then incubated at room temperature. After 3 hours, a 15 µl aliquot was removed and evaluated by RP-HPLC and ESI-MS. This process was repeated until significant levels of reaction were detected by formation of single-labeled SA-lysine test peptide products.

Selective Labeling of LY-(SAOD)-AGCRANK-NH$_2$ and LY-(SAOD)-AGCEYRIDRVR-LFVDKLDNIAQVPRV-GAA-HHHHHH with Tetramethylrhodamine N-hydroxysuccinimidyl Ester. A sample of 20 µL of LY-(SAOD)-AGCRANK-NH$_2$ (2.5 µg/µl, 2.18 mM) in 200 mM citrate buffer, pH=4.7, 5 mM TCEP was labeled using 4.3 equivalents of dye in DMSO, purified and analyzed. Expected Mass=1580, Observed Mass=1580. A 20 µL sample of LY-(SAOD)-AGCEYRIDRVRLFVDKLDNIAQVPRV-GAA-HHHHH (SEQ ID>NO: 12) (9.7 µg/µl, 2.12 mM) in 200 mM citrate buffer, pH=4.7, containing 5 mM TCEP and 3M guanidine hydrochloride was labeled using a modified procedure. 18 µl of a solution of tetramethylrhodamine N-hydroxysuccinimide (10 µg/µl) in DMSO was added in 6 µl aliquots over 15 minutes with rapid mixing. The reaction was incubated at room temperature for 5 hours prior to gel filtration/RP-HPLC purification and mass spectral analysis. Expected Mass=4930, Observed Mass=4929.

Labeling of β-Lactoglobulin with Tetramethylrhodamine N-hydroxysuccinimide ester: 10 µL of a 10 mg/ml solution of tetramethylrhodamine N-hydroxysuccinimide ester in DMSO (9.5 equivalents compared to protein), was added to a solution containing 10 µL of DMSO and 20 µL of a solution of β-Lactoglobulin (20.3 mg/ml or 1.1 mM) in 2.8 M guanidine hydrochloride with 5 mM TCEP (pH 4.7). After 3 hours, protein was separated from unreacted dye by gel filtration, and labeling was determined by analysis of the dye-to-protein ratio (protein concentration was determined by the method of Waddel and ε for tetramethylrhodamine in phosphate buffer, pH=8.0 of 81,000).

Labeling of PBD Proteins with Alexa-532 N-Hydroxysuccinimide Ester: 150 µg of the SAOD-modified PBD protein was dissolved in 105 µL of 200 mM sodium citrate buffer, pH=4.8, containing 5 mM TCEP (protein concentration ~0.28 mM). A solution of Alexa-532-OSu in DMSO (dye concentration ~10 mg/ml in DMSO) was titrated into the protein solution in 5 µL aliquots over 72 hours. Four hours after each addition, the extent of labeling was determined by RP-HPLC and MS. Labeling was continued until quantities of double-labeled PBD was obtained (SAOD-modified PBD). Alexa-532 labeled SAOD-modified PBD, Mass Expected=5871, Mass Observed=5870.

Zinc/Acetic Acid Reduction of the N-methylaminooxy N—O Bond in Peptides. Reductive cleavage of the N—O bond was performed using zinc and aqueous acetic acid. Effervescence in the reaction was evident after a few seconds and subsided after 60-120 minutes. After 14 hours, the reaction supernatant was analyzed by RP-HPLC and ESI-MS. Reduction of labeled SA-Test peptide, Expected Mass=1530, Observed Mass=1530: Reduction of labeled (SAOD)-AGCRANK—NH$_2$: Expected Mass=1139, Observed Mass=1139.

Trypsin/Chymotrypsin Cleavage of Labeled LY-(SAOD)-AGCEYRIDRVRLiFVDKLDN-IAQVPRVGAA-HHH-HHH Peptide. 10 µl of a 0.05 mg/ml solution of either trypsin or α-chymotrypsin in 25 mM ammonium carbonate (without pH adjustment) was added to 5 µl of a 10-20 µg/µl solution of pure tetramethylrhodamine-labeled peptide in water (final concentration of protease is 0.033 mg/ml). The reaction was incubated at room temperature for 24 hours prior to analysis of peptide fragments by MALDI-MS.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A peptide conjugate of formula (III):

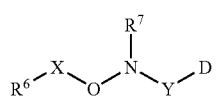

wherein $R^6$ is a peptide;

X is a direct bond or a linking group;

$R^7$ is $(C_1\text{-}C_6)$alkyl;

Y is a direct bond or a linking group; and

D is a biophysical probe, wherein the biophysical probe is a fluorescent group.

2. The peptide conjugate of claim 1 wherein $R^6$ is an antibody.

3. The peptide conjugate of claim 1 wherein $R^6$ comprises about 2 to about 1000 amino acids.

4. The peptide conjugate of claim 1 wherein $R^6$ comprises about 5 to about 500 amino acids.

5. The peptide conjugate of claim 1 wherein $R^6$ comprises about 10 to about 100 amino acids.

6. The peptide conjugate of claim 1 wherein X is about 5 angstroms to about 100 angstroms in length.

7. The peptide conjugate of claim 1 wherein X is about 5 angstroms to about 25 angstroms in length.

8. The peptide conjugate of claim 1 wherein X is —$R_a$—C(=O)—NH—$R_b$— wherein each of $R_a$ and $R_b$ is independently $(C_1\text{-}C_6)$alkylene.

9. The peptide conjugate of claim 8 wherein each of $R_a$ and $R_b$ is methylene (—$CH_2$—).

10. The peptide conjugate of claim 1 wherein $R^7$ is methyl.

11. The peptide conjugate of claim 1 wherein Y is about 5 angstroms to about 100 angstroms in length.

12. The peptide conjugate of claim 1 wherein Y is about 5 angstroms to about 25 angstroms in length.

13. The peptide conjugate of claim 1 wherein Y is $(C_1\text{-}C_6)$alkylene.

14. The peptide conjugate of claim 1 wherein Y is methylene (—$CH_2$—).

15. The peptide conjugate of claim 1 wherein the fluorescent group is an Alexa dye, a solvatochromic dye, an electrochromatic dye, or a dye that is sensitive to pH change, or ligand binding.

16. The peptide conjugate of claim 1 wherein D is Alexa-532, hydroxycoumarin, aminocoumarin, methoxycoumarin, amino methylcoumarin, pyrenyloxytrisulfonic acid, 3,6-disulphonated 4-aminonaphthalimide, 4-chloro-7-nitrobenz-2-oxa-1,3-diazole, P-phycoerythrin, R-phycoerythrin, phycoerythrin, fluorescein, tetramethylrhodamine-5-isothiocyanate, tetramethylrhodamine-6-isothiocyanate, X-rhodamine, lissamine rhodamine B, peridinin chlorophyll protein, Texas Red, allophycocyanin, 2',7'-difluorofluorescein, tetramethylrhodamine, dansyl, Indo-1,

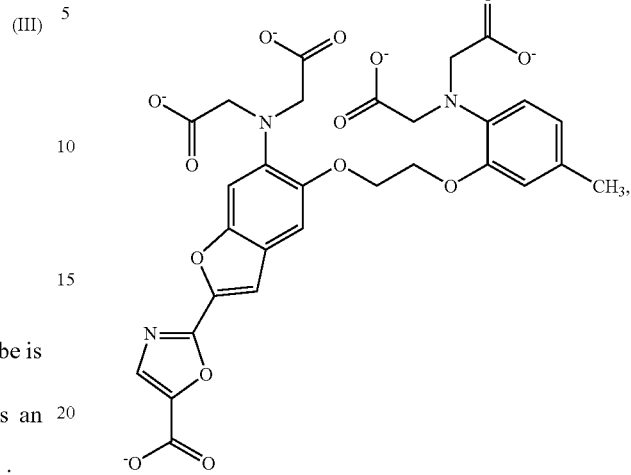

fura-2

1,1'dioctadecyl-3,3,3',3'-tetramethlindocarbocyanine perchlorate,

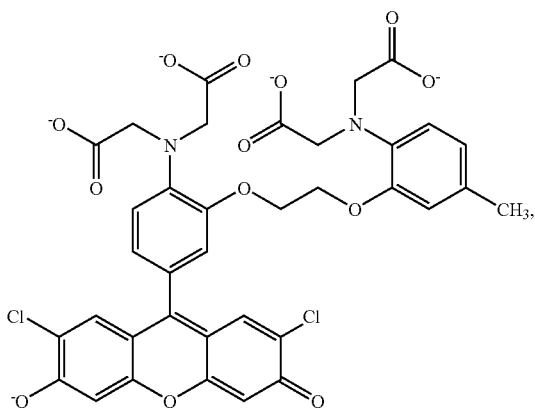

Fluo-3 dichlorofluorescin, dihydrorhodamine, monochlorobimane, or calcein.

17. The peptide conjugate of claim 1 wherein:

$R^6$ is SEQ ID NO: 1;

X is $R_a$—C(=O)CH(NH$_2$)CH$_2$N(H)C(=O)CH$_2$—$R_b$; wherein $R_a$ is a direct bond to the amino terminus of $R_6$ and wherein $R_b$ is a direct bond to the oxygen of the aminooxy group of formula (III);

$R^7$ is methyl;

Y is a direct bond; and

D is Alexa-532.

18. A peptide conjugate of formula (IV):

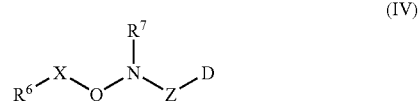

wherein
- $R^6$ is a peptide;
- X is a direct bond or a linking group;
- $R^7$ is $(C_1\text{-}C_6)$alkyl;
- Z is a single or double bond between N and D; and
- D is a biophysical probe, wherein the biophysical probe is a fluorescent group.

19. An isolated peptide consisting essentially of a backbone and one or more protected secondary aminooxy groups, wherein the protected aminooxy group is on an amino acid side chain, the protected aminooxy group is protected with an amino protecting group and is unreactive during Boc solid-phase peptide synthesis, and a substituent on the aminooxy group is $(C_1\text{-}C_6)$alkyl; and wherein the backbone of the peptide further comprises —C=N—O—CH$_2$—C(=O)—.

20. The peptide of claim 19, wherein the N-terminus of the peptide further comprises an aminooxy group.

21. A method for preparing a peptide conjugate comprising reacting a peptide of the formula (VI)

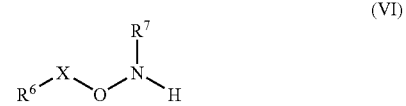

(VI)

wherein
- $R^6$ is a peptide;
- X is a direct bond or a linking group;
- $R^7$ is $(C_1\text{-}C_6)$alkyl;

with a fluorescent molecule having an electrophilic moiety that is reactive with the aminooxy groups(s) to provide the peptide conjugate.

* * * * *

UNITED STATES PATENT AND TRADEMARK OFFICE
CERTIFICATE OF CORRECTION

PATENT NO.       : 7,351,797 B1
APPLICATION NO.  : 10/381903
DATED            : April 1, 2008
INVENTOR(S)      : Klaus M. Hahn and Steven J. Bark It is certified that error appears in the above-identified patent and that said Letters Patent is hereby corrected as shown below:

On title page, item (56), under "Other Publications", in column 1, line 3, delete "Hightly" and insert -- Highly --, therefor.

On title page, item (56), under "Other Publications", in column 2, line 15, delete "Chemselective" and insert -- Chemoselective --, therefor.

On title page, item (56), under "Other Publications", in column 2, line 19, delete "Weinhem," and insert -- Weinheim, --, therefor.

In column 1, line 39, delete "1995,24" and insert -- 1995, 24 --, therefor.

In column 1, line 43, delete "1990,265" and insert -- 1990, 265 --, therefor.

In column 1, line 47, after "solution" insert -- ( --.

In column 1, line 52, delete "57745779;" and insert -- 5774-5779; --, therefor.

In column 2, line 17, delete "Ann." and insert -- Am. --, therefor.

In column 2, line 48, delete "C" and insert -- $C^{\alpha}$ --, therefor.

In column 3, line 49, after "($C_1$-$C_6$)" delete "alyl," and insert -- alkyl, --, therefor.

In column 3, line 66, delete "electrophylic" and insert -- electrophilic --, therefor.

In column 4, line 8, after "thioester" delete "," and insert -- ; --, therefor.

In column 4, line 25, after "radical" delete "," and insert -- ; --, therefor.

In column 4, line 47, delete "Sythesis;" and insert -- Synthesis; --, therefor.

In column 5, line 21, delete "enviornmental" and insert -- environmental --, therefor.

In column 5, line 67, after "naphthyl" delete ";" and insert -- . --, therefor.

In column 6, line 40, delete "$R_b$-is" and insert -- $R_b$ is --, therefor.

UNITED STATES PATENT AND TRADEMARK OFFICE
CERTIFICATE OF CORRECTION

PATENT NO. : 7,351,797 B1
APPLICATION NO. : 10/381903
DATED : April 1, 2008
INVENTOR(S) : Klaus M. Hahn and Steven J. Bark It is certified that error appears in the above-identified patent and that said Letters Patent is hereby corrected as shown below:

In column 6, line 46, delete "Specificaly" and insert -- Specifically --, therefor.

In column 6, line 61, delete "R-Phycoerthrin," and insert -- R-Phycoerythrin, --, therefor.

In column 6, line 65, delete "APCy7" and insert -- APC-Cy7 --, therefor.

In column 6, line 67, delete "FM 143," and insert -- FM 1-43, --, therefor.

In column 7, line 1, delete "lndo-1," and insert -- Indo-1, --, therefor.

In column 7, line 7, delete "Hoerchst" and insert -- Hoechst --, therefor.

In column 7, line 8, delete "Etkhidium" and insert -- Ethidium --, therefor.

In column 8, line 39, after "Opin" insert -- . --.

In column 8, line 47, delete "bond O–" and insert -- bond –O– --, therefor.

In column 8, line 62, delete "functionalised" and insert -- functionalized --, therefor.

In column 10, line 25, delete "$C_2H$" and insert -- $CO_2H$ --, therefor.

In column 10, line 38, delete "50%oDMSO" and insert -- 50%DMSO --, therefor.

In column 11, line 7, delete "CTCEP)," and insert -- (TCEP), --, therefor.

In column 11, line 52, delete "systern," and insert -- system, --, therefor.

In column 11, line 55, delete "another.0.5" and insert -- another 0.5 --, therefor.

In column 11, line 58, after "product" insert -- . --.

In column 11, line 65, delete "nucleophicity" and insert -- nucleophilicity --, therefor.

In column 11, line 66, after "an" delete "an".

UNITED STATES PATENT AND TRADEMARK OFFICE
CERTIFICATE OF CORRECTION

PATENT NO. : 7,351,797 B1
APPLICATION NO. : 10/381903
DATED : April 1, 2008
INVENTOR(S) : Klaus M. Hahn and Steven J. Bark It is certified that error appears in the above-identified patent and that said Letters Patent is hereby corrected as shown below:

In column 12, line 1, delete "O-alkylaminooxy" and insert -- O-alkyl aminooxy --, therefor.

In column 12, line 16, delete "C" and insert -- $C^\alpha$ --, therefor.

In column 12, line 18-19, delete "Proteins by Total Chemical Synthesis Often Requires" and insert -- proteins by total chemical synthesis often requires --, therefor.

In column 12, line 38, delete "Cl-Z(SA)" and insert -- Cl-Z-(SA) --, therefor.

In column 12, line 46, after "press)" insert -- . --.

In column 13, line 59, delete "quantitiation)" and insert -- quantitation) --, therefor.

In column 13, line 61, delete "difficull" and insert -- difficult. --, therefor.

In column 14, line 16, delete "semipreperative" and insert -- semipreparative --, therefor.

In column 14, line 25, delete "API-I" and insert -- API-III --, therefor.

In column 14, line 25, delete "quadruple" and insert -- quadrupole --, therefor.

In column 14, line 28, delete "(Ihermo" and insert -- (Thermo --, therefor.

In column 14, line 32, delete "molecularspecies" and insert -- molecular species --, therefor.

In column 14, line 35, delete "hydroxycinnammic" and insert -- hydroxycinnamic --, therefor.

In column 14, line 35-36, delete "sinipinic" and insert -- sinapinic --, therefor.

In column 14, line 48, delete "[[4" and insert -- [[4– --, therefor.

In column 14, line 66, delete "Parn," and insert -- Pam, --, therefor.

UNITED STATES PATENT AND TRADEMARK OFFICE
CERTIFICATE OF CORRECTION

PATENT NO. : 7,351,797 B1
APPLICATION NO. : 10/381903
DATED : April 1, 2008
INVENTOR(S) : Klaus M. Hahn and Steven J. Bark It is certified that error appears in the above-identified patent and that said Letters Patent is hereby corrected as shown below:

In column 14, line 67, delete "BulL" and insert -- Bull. --, therefor.

In column 15, line 1, after "Acad" insert -- . --.

In column 15, line 10-25, delete "Synthesis of TAMPAL Resin (Hojo, H., et al., Bull. Chem. Soc. Jpn. 1993, 66:2700-2706). 2.5 grams of MBHA resin (0.865 mmol/g, 2.16 mmol of amine) was swelled in DMF. Boc-Leu-OH (1.1 grams, 4.4 mmol) was activated with HBTU (8 ml, 0.5M solution) and DIEA (2 ml), then coupled to the MBHA resin until complete reaction by ninhydrin assay. The $N^{\alpha}$-Boc group of the linked leucine was removed with neat TFA, then S-trt-$\beta$-mercaptopropionic acid (1.5 grams, 4.3 mmol), activated in the same manner as Boc-Leu-OH, was added to the deprotected Leu-MBHA resin and allowed to couple until complete reaction. The S-Trt-$\beta$-mercaptopropionyl-Leu-MBHA resin was washed extensively with DMF, then DCM/MeOH (1/1), and finally dried in vacuo to yield 3.39 grams of thioester resin. Substitution calculated by weight gain yielded 0.549 mmol/gram." and insert the same on Col. 15, Line 11, below "RP-HPLC." as a new Paragraph.

In column 15, line 22, delete "DCMIMeOH" and insert -- DCM/MeOH --, therefor.

In column 15, line 39, delete "2°" and insert -- 2- --, therefor.

In column 15, line 42, delete "stining" and insert -- stirring --, therefor.

In column 15, line 50, delete "(s, 21)," and insert -- (s, 2H), --, therefor.

In column 16, line 3, delete "acetatelacetic" and insert --acetate/acetic --, therefor.

In column 16, line 13, delete "temprature." and insert -- temperature. --, therefor.

In column 16, line 16, delete "(30.2$^8$" and insert -- (3.28 --, therefor.

In column 16, line 17, delete "80120/1)." and insert -- 80/20/1). --, therefor.

In column 16, line 18, delete "728" and insert -- 7.28 --, therefor.

In column 16, line 19, delete "(m, 21H)." and insert -- (m, 2H). --, therefor.

UNITED STATES PATENT AND TRADEMARK OFFICE
CERTIFICATE OF CORRECTION

PATENT NO. : 7,351,797 B1
APPLICATION NO. : 10/381903
DATED : April 1, 2008
INVENTOR(S) : Klaus M. Hahn and Steven J. Bark It is certified that error appears in the above-identified patent and that said Letters Patent is hereby corrected as shown below:

In column 16, line 50, delete "NHrAIKAARAAAAK*RACA-CO$_2$K," and insert -- NH$_2$-AKAARAAAAK*AARACA-CO$_2$H, --, therefor.

In column 17, line 31, delete "VRLPFVDKLCNIAQ" and insert -- VRLPFVDKLDNIAQ --, therefor.

In column 17, line 37-38, delete "KKKEKERPEISLPSDFEHIVGFDA" and insert -- KKKEKERPEISLPSDFEHTIHVGFDA --, therefor.

In column 17, line 42-43, delete "KKKPEKERPEISLPSDFEHITHIVGFDA" and insert -- KKKEKERPEISLPSDFEHTIHVGFDA --, therefor.

In column 17, line 53-54, delete "KEKERPEISLPSDFEHIVGFDA" and insert -- KKKEKERPEISLPSDFEHTIHVGFDA --, therefor.

In column 17, line 55, delete "KKKEISLPSDFEHTHVG" and insert -- KKKEKERPEISLPSDFEHTIHVG --, therefor.

In column 17, line 57, delete "CTGEF=GMPEQWARLLQT," and insert -- CTGEFTGMPEQWARLLQT, --, therefor.

In column 18, line 14, delete "ESI MS." and insert -- ESI-MS. --, therefor.

In column 18, line 17, delete "N-hydroxysuccimide" and insert -- N-hydroxysuccinimide --, therefor.

In column 18, line 38, after "GAA-" delete "HHHHH" and insert -- HHHHHH --, therefor.

In column 20, line 2, delete "AGCEYRIDRVRLiFVDKLDN" and insert -- AGCEYRIDRVRLFVDKLDN --, therefor.

In column 26, line 47, in Claim 16, delete "dichlorofluorescin," and insert -- dichlorofluorescein, --, therefor.

UNITED STATES PATENT AND TRADEMARK OFFICE
CERTIFICATE OF CORRECTION

PATENT NO. : 7,351,797 B1
APPLICATION NO. : 10/381903
DATED : April 1, 2008
INVENTOR(S) : Klaus M. Hahn and Steven J. Bark It is certified that error appears in the above-identified patent and that said Letters Patent is hereby corrected as shown below:

In column 26, line 52, in Claim 17, delete "$R_6$" and insert -- $R^6$ --, therefor.

In column 28, line 2, in Claim 21, after "(VI)" insert -- : --.

In column 28, line 15, in Claim 21, delete "groups(s)" and insert -- group(s) --, therefor.

Signed and Sealed this

Twenty-ninth Day of July, 2008

JON W. DUDAS
*Director of the United States Patent and Trademark Office*